US012257086B2

(12) United States Patent
Ferrari et al.

(10) Patent No.: US 12,257,086 B2
(45) Date of Patent: Mar. 25, 2025

(54) ARRANGEMENT FOR SECURING A ROBOTIC SYSTEM TO A PATIENT TABLE

(71) Applicant: Corindus, Inc., Newton, MA (US)

(72) Inventors: Natalie Ferrari, Waltham, MA (US); Dino Kasvikis, Barrington, RI (US); Eric Klem, Lexington, MA (US); Kyle McKenney, Westwood, MA (US); Anthony Clegg Parker, New Ipswich, NH (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 0 days.

(21) Appl. No.: 18/054,733

(22) Filed: Nov. 11, 2022

(65) Prior Publication Data
US 2024/0156421 A1    May 16, 2024

(51) Int. Cl.
*A61B 6/04* (2006.01)
*A61B 34/30* (2016.01)
*A61G 13/02* (2006.01)

(52) U.S. Cl.
CPC ............ *A61B 6/0407* (2013.01); *A61B 34/30* (2016.02); *A61G 13/02* (2013.01); *A61B 2034/304* (2016.02)

(58) Field of Classification Search
CPC ......... A61B 6/04; A61B 6/0407; A61B 34/30; A61B 2034/304; A61G 13/02
See application file for complete search history.

(56) References Cited

U.S. PATENT DOCUMENTS

| | | | |
|---|---|---|---|
| 1,862,237 A * | 6/1932 | Pepler | A47B 23/02 211/119.006 |
| 3,821,525 A | 6/1974 | Eaton et al. | |
| 3,823,709 A | 7/1974 | McGuire | |
| 4,616,813 A | 10/1986 | McConnell | |
| 5,287,575 A * | 2/1994 | Allen | A61G 13/101 5/507.1 |
| 5,312,338 A | 5/1994 | Nelson et al. | |
| 5,350,101 A | 9/1994 | Godlewski | |
| 6,478,028 B1 | 11/2002 | Paolitto et al. | |
| 6,558,371 B2 | 5/2003 | Dorn | |

(Continued)

FOREIGN PATENT DOCUMENTS

| CN | 115670663 | 2/2023 |
|---|---|---|
| CN | 115670664 | 2/2023 |

(Continued)

OTHER PUBLICATIONS

Ergonomic Guidelines for Manual Material Handling, DHHS (NIOSH), Apr. 2007.

*Primary Examiner* — Fredrick C Conley

(57) ABSTRACT

A table attach support is configured to secure a medical device to a patient table having a patient supporting surface. The table attach support comprises: a first engagement mechanism including an attachment mechanism and a locking mechanism; a second engagement mechanism; and an extension member extending between the first engagement mechanism and the second engagement mechanism. The attachment mechanism is configured to actuate from a first position to a second position to secure the table attach support to the patient table. The locking mechanism is configured to lock the attachment mechanism in the second position.

20 Claims, 23 Drawing Sheets

(56) References Cited

U.S. PATENT DOCUMENTS

| | | |
|---|---|---|
| 7,331,967 B2 | 2/2008 | Lee et al. |
| 7,766,856 B2 | 8/2010 | Ferry et al. |
| 7,766,894 B2 | 8/2010 | Weitzner et al. |
| 7,789,874 B2 | 9/2010 | Yu et al. |
| 7,822,466 B2 | 10/2010 | Stoianovici et al. |
| 7,972,298 B2 | 7/2011 | Wallace et al. |
| 8,052,636 B2 | 11/2011 | Moll et al. |
| 8,092,397 B2 | 1/2012 | Wallace et al. |
| 8,146,599 B2 | 4/2012 | Wilson et al. |
| 8,146,874 B2 | 4/2012 | Yu |
| 8,343,096 B2 | 1/2013 | Kirschenman et al. |
| 8,449,449 B2 | 5/2013 | Haarstad et al. |
| 8,617,102 B2 | 12/2013 | Moll et al. |
| 8,684,952 B2 | 4/2014 | Weitzner et al. |
| 8,708,952 B2 | 4/2014 | Cohen et al. |
| 8,736,212 B2 | 5/2014 | Sandhu et al. |
| 8,747,309 B2 | 6/2014 | Viola |
| 8,801,661 B2 | 8/2014 | Moll et al. |
| 8,974,408 B2 | 3/2015 | Wallace et al. |
| 8,986,246 B2 | 3/2015 | Foley et al. |
| 9,283,046 B2 | 3/2016 | Walker et al. |
| 9,326,822 B2 | 5/2016 | Lewis et al. |
| 9,408,669 B2 | 8/2016 | Kokish et al. |
| 9,566,201 B2 | 2/2017 | Yu |
| 9,750,657 B2 * | 9/2017 | Drake ................. A61G 13/128 |
| 9,782,564 B2 | 10/2017 | Zirps et al. |
| 9,814,864 B2 | 11/2017 | Scarpine et al. |
| 9,820,819 B2 | 11/2017 | Olson |
| 9,825,455 B2 | 11/2017 | Sandhu et al. |
| 9,974,619 B2 | 5/2018 | Goldenberg et al. |
| 10,159,533 B2 | 12/2018 | Moll et al. |
| 10,213,264 B2 | 2/2019 | Tanner et al. |
| 10,307,214 B2 | 6/2019 | Lathrop et al. |
| 10,376,672 B2 | 8/2019 | Yu |
| 10,448,859 B2 | 10/2019 | Wehner et al. |
| 10,667,875 B2 | 6/2020 | DeFonzo et al. |
| 10,702,348 B2 | 7/2020 | Moll et al. |
| 10,952,914 B1 * | 3/2021 | Miller ................. A61G 13/1245 |
| 11,013,574 B1 | 5/2021 | Gomez et al. |
| 2002/0177789 A1 | 11/2002 | Ferry et al. |
| 2004/0133979 A1 * | 7/2004 | Newkirk ................. A61F 5/3761 5/624 |
| 2004/0176751 A1 * | 9/2004 | Weitzner ................. A61B 34/32 606/1 |
| 2004/0254566 A1 | 12/2004 | Plicchi et al. |
| 2007/0060879 A1 | 3/2007 | Weitzner et al. |
| 2008/0214592 A1 | 9/2008 | Wilson et al. |
| 2008/0243064 A1 | 10/2008 | Stahler et al. |
| 2008/0245946 A1 * | 10/2008 | Yu ................. A61B 34/20 248/637 |
| 2009/0082722 A1 | 3/2009 | Munger et al. |
| 2009/0308400 A1 * | 12/2009 | Wilson ................. A61B 90/57 128/845 |
| 2012/0071752 A1 | 3/2012 | Sewell et al. |
| 2014/0276389 A1 | 9/2014 | Walker |
| 2015/0142013 A1 | 5/2015 | Tanner et al. |
| 2015/0366433 A1 | 12/2015 | Atarot et al. |
| 2017/0007343 A1 | 1/2017 | Yu |
| 2017/0196477 A1 * | 7/2017 | Wehner ................. A61B 5/05 |
| 2017/0304021 A1 | 10/2017 | Hathaway |
| 2017/0348060 A1 | 12/2017 | Blacker |
| 2018/0132951 A1 | 5/2018 | Olson |
| 2018/0207794 A1 | 7/2018 | Sebring et al. |
| 2019/0175887 A1 | 6/2019 | Shameli |
| 2020/0008997 A1 | 1/2020 | Dalbert |
| 2020/0069333 A1 | 3/2020 | Ahluwalia et al. |
| 2020/0085342 A1 | 3/2020 | Wehner et al. |
| 2020/0085516 A1 | 3/2020 | DeFonzo et al. |
| 2020/0163733 A1 | 5/2020 | Smith et al. |
| 2020/0188043 A1 | 6/2020 | Yu et al. |
| 2020/0323596 A1 | 10/2020 | Moll et al. |
| 2021/0093407 A1 | 4/2021 | Frederiskson et al. |
| 2023/0035163 A1 | 2/2023 | Klem et al. |

FOREIGN PATENT DOCUMENTS

| | | |
|---|---|---|
| EP | 1560527 | 10/2008 |
| EP | 2124800 | 12/2009 |
| EP | 1980212 | 5/2011 |
| EP | 2893898 | 3/2017 |
| EP | 3072472 | 8/2017 |
| WO | 0143592 | 6/2001 |
| WO | 2011155411 | 12/2011 |
| WO | WO-2011155411 A1 * | 12/2011 ......... A61B 1/00149 |
| WO | 2018147930 | 8/2018 |
| WO | 2019227129 | 12/2019 |
| WO | 2020002749 | 1/2020 |
| WO | 2020020432 | 1/2020 |
| WO | 2021003275 | 1/2021 |
| WO | 2021011518 | 1/2021 |
| WO | 2021011533 | 1/2021 |
| WO | 2021011551 | 1/2021 |
| WO | 2021011554 | 1/2021 |

* cited by examiner

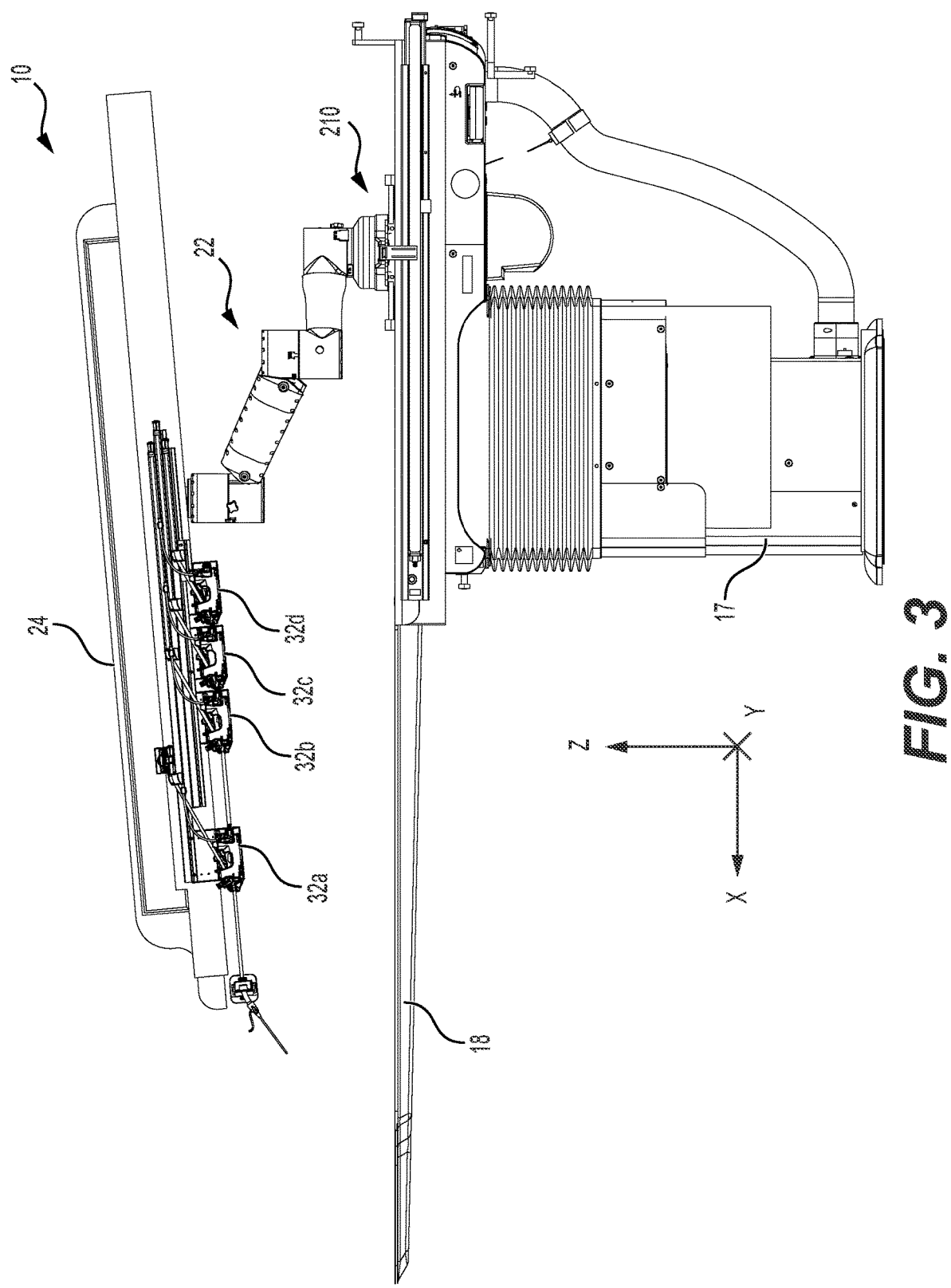

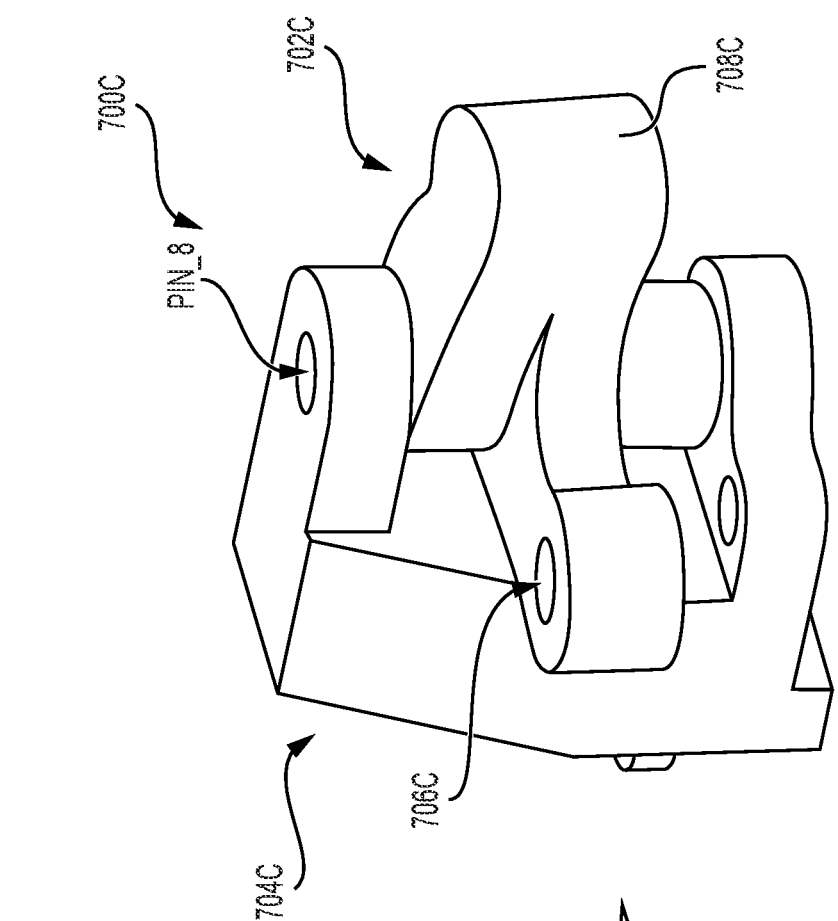
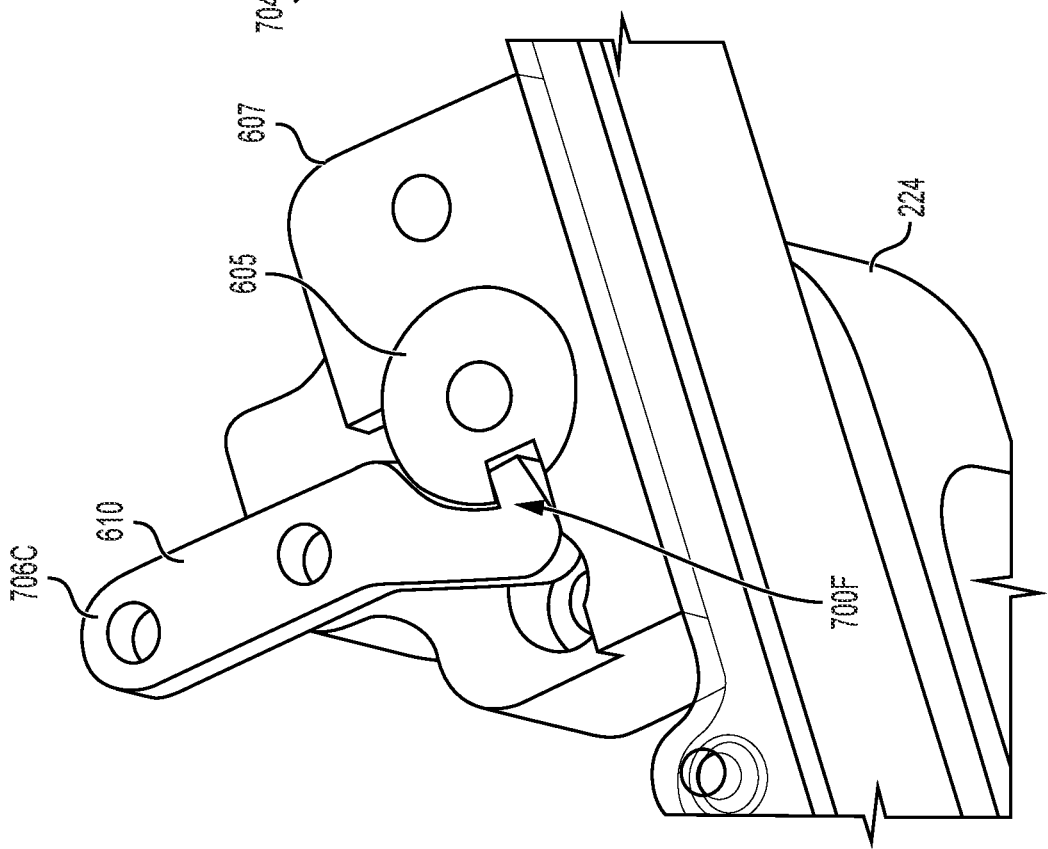
FIG. 9B
FIG. 9A

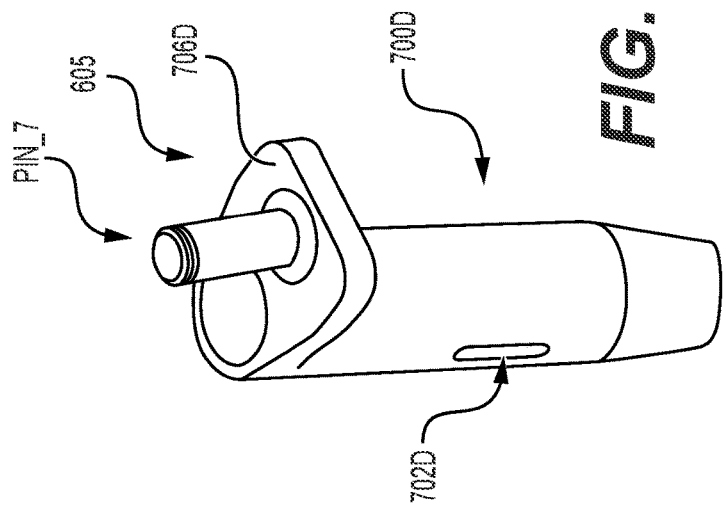
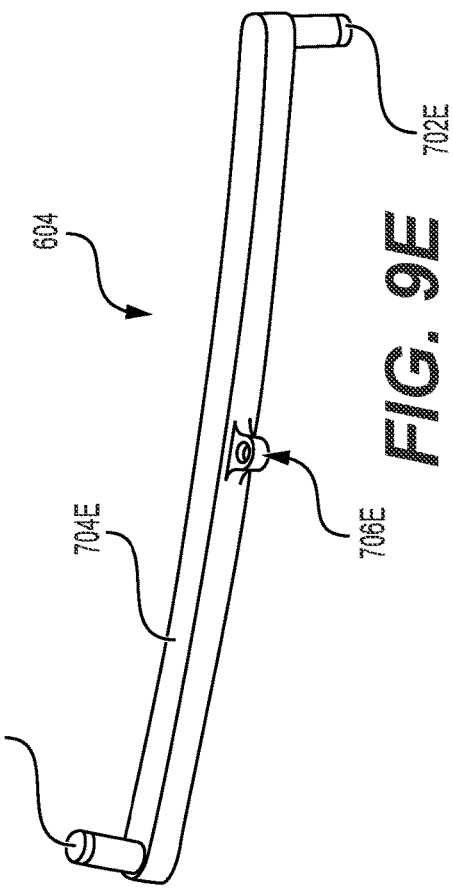
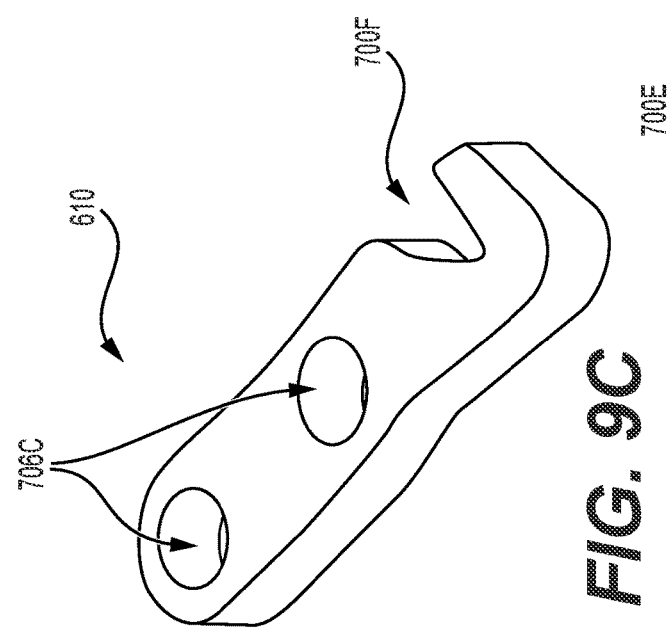

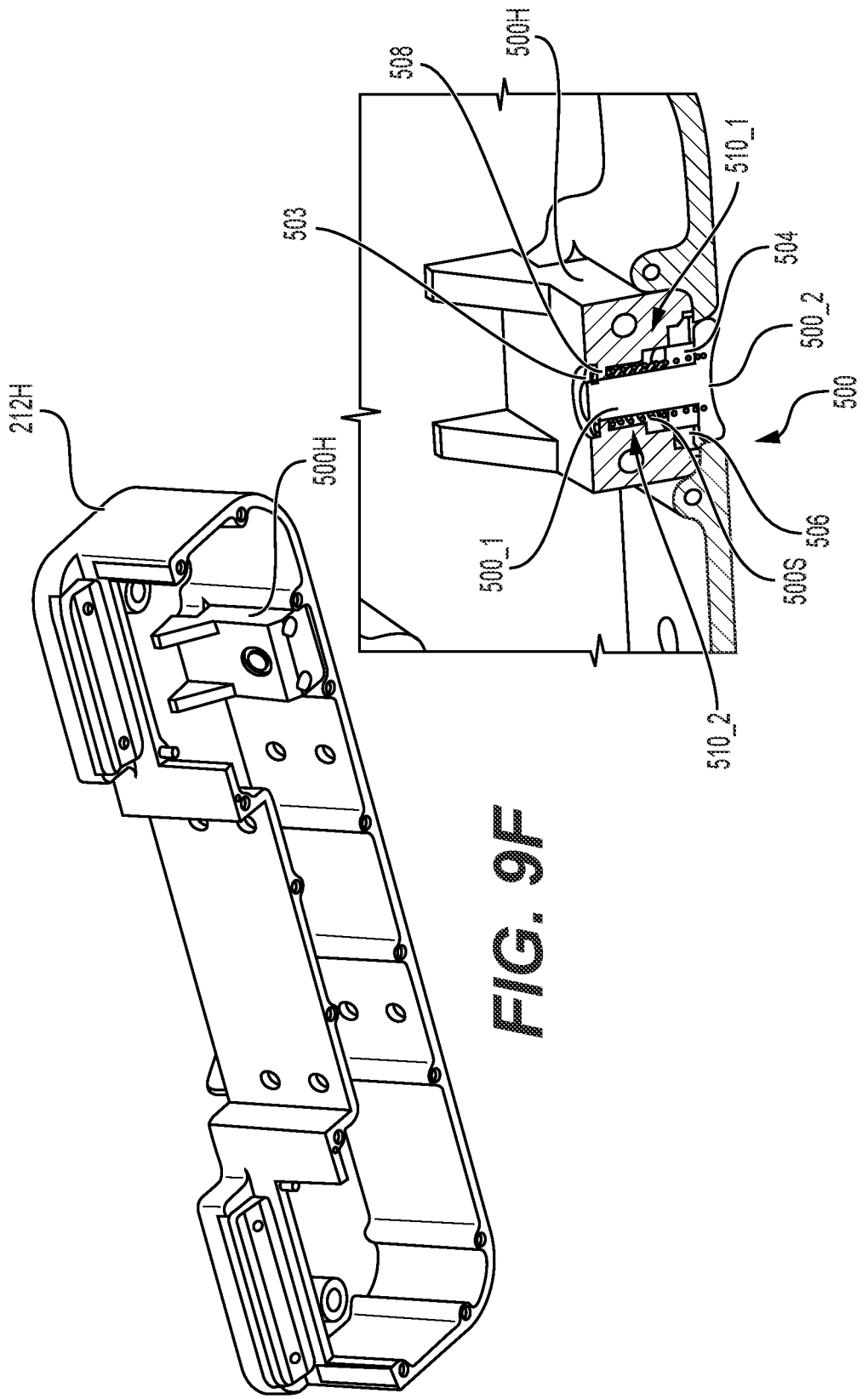

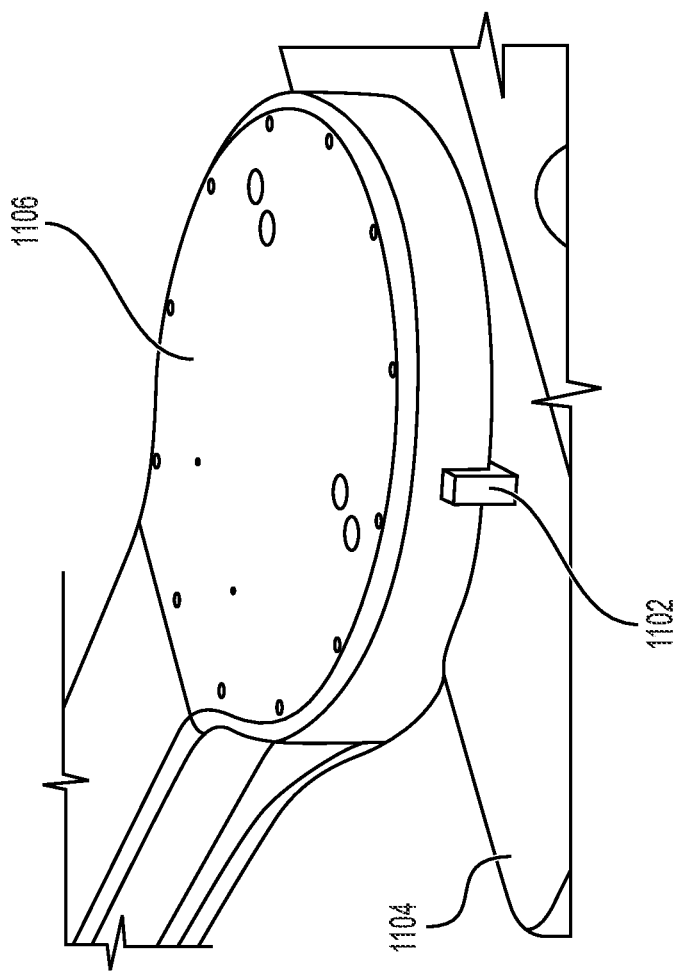
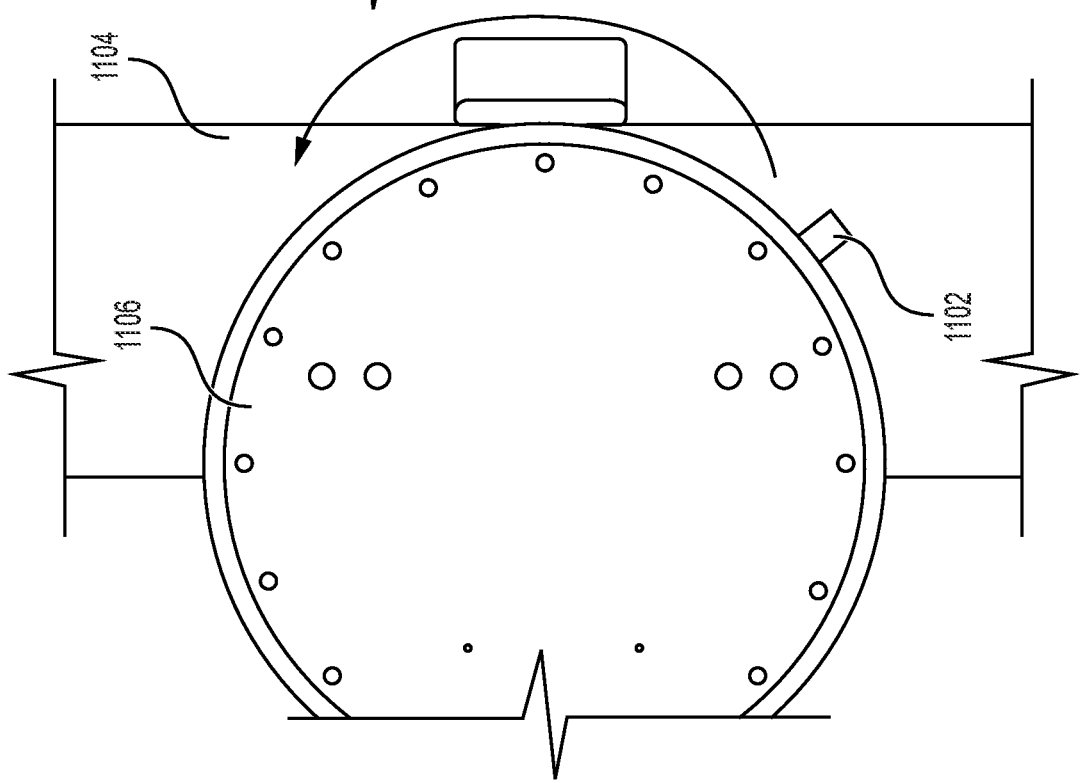

ations to secure robotic systems to patient tables, positioning
ARRANGEMENT FOR SECURING A ROBOTIC SYSTEM TO A PATIENT TABLE

FIELD

One or more example embodiments relate to arrangements to secure robotic systems to patient tables, positioning systems including arrangements to secure robotic systems, and robotic systems (e.g., robotic medical procedure systems) including the same.

BACKGROUND

Catheters and other elongated medical devices (EMDs) may be used for minimally-invasive medical procedures for diagnosing and/or treating diseases of various vascular systems. Example medical procedures include neurovascular intervention (NVI) also known as neurointerventional surgery, percutaneous coronary intervention (PCI) and peripheral vascular intervention (PVI). These procedures typically involve navigating a guidewire through the vasculature to advance a catheter to deliver therapy. Robotic catheter-based procedure systems may be used to aid a physician in performing medical procedures such as those mentioned above.

SUMMARY

At least one example embodiment provides a table attach support to secure a medical device (e.g., a robotic catheter-based medical procedure device) to a patient table having a patient supporting surface. The table attach support comprises: a first engagement mechanism including an attachment mechanism and a locking mechanism; a second engagement mechanism; and an extension member extending between the first engagement mechanism and the second engagement mechanism. The attachment mechanism is configured to actuate from a first position to a second position to secure the table attach support to the patient table. The locking mechanism is configured to lock the attachment mechanism in the second position.

At least one other example embodiment provides a method for securing a table attach support and/or medical device (e.g., a robotic catheter-based medical procedure device) to a patient table having a patient supporting surface, wherein the table attach support includes a first engagement mechanism, a second engagement mechanism, and an extension member extending between the first engagement mechanism and the second engagement mechanism, wherein the first engagement mechanism includes an attachment mechanism and a locking mechanism, and wherein the method comprises: actuating the attachment mechanism from a first position to a second position to secure the table attach support to the patient table; and locking the attachment mechanism in the second position via the locking mechanism.

At least one other example embodiment provides a medical device (e.g., a robotic catheter-based medical procedure device) comprising: a robotic drive; a positioning system configured to support the robotic drive; and table attach support configured to support the positioning system, and to secure the medical device to a patient table having a patient supporting surface. The table attach support includes: a first engagement mechanism including an attachment mechanism and a locking mechanism; a second engagement mechanism; and an extension member extending between the first engagement mechanism and the second engagement mechanism. The attachment mechanism is configured to actuate from a first position to a second position to secure the table attach support to the patient table. The locking mechanism is configured to lock the attachment mechanism in the second position.

According to one or more example embodiments, the locking mechanism may include a release button configured to unlock the attachment mechanism to actuate from the second position to the first position to disengage the table attach support from the patient table.

The attachment mechanism may include: a first roller cam assembly; a second roller cam assembly; and a linkage assembly operatively coupled to the first roller cam assembly and the second roller cam assembly. The linkage assembly may be configured to cause the first roller cam assembly and the second roller cam assembly to move in opposite directions during actuation from the first position to the second position or from the second position to the first position.

The locking mechanism may include a crank lock assembly engaged with the linkage assembly.

The table attach support may include a handle engaged with the crank lock assembly, wherein the handle is configured to cause the attachment mechanism to actuate from the first position to the second position or from the second position to the first position.

The crank lock assembly may be configured to: translate movement of the handle into movement of the attachment mechanism to move the attachment mechanism between the first position and the second position; and lock the attachment mechanism in the second position.

The crank lock assembly may include a crank and a lock hook. The crank may have a longitudinal shaft portion and a flange portion engaged with the linkage assembly. The longitudinal shaft portion may have a notch, and the crank may be configured to translate the movement of the handle into the movement of the attachment mechanism. The lock hook may be configured to engage with the notch to lock the attachment mechanism in the second position.

The notch may be on a surface of the longitudinal shaft portion of the crank.

The locking mechanism may include a lock button assembly and a lock linkage configured to disengage the lock hook from the notch to unlock the attachment mechanism thereby allowing movement from the second position to the first position.

The crank lock assembly may include a body member having a cylindrical hole and a slot. The cylindrical hole may be configured to receive the longitudinal shaft portion of the crank, and the slot may be configured to receive the lock hook. The lock hook may be pivotably secured in the slot via a pin.

The lock hook may be configured to pivot about the pin to move between an engaged position and a disengaged position with respect to the notch. In the engaged position, the lock hook is engaged with the notch, whereas in the disengaged position, the lock hook is disengaged from the notch.

The lock button assembly may include: a release button; and a rocker mount engaged with the lock linkage. The rocker mount may be configured to translate pressing of the release button into force exerted on the lock linkage. The lock linkage may be pivotably engaged with the lock hook. The lock linkage may be configured to cause the lock hook to pivot in response to the force exerted by the rocker mount.

The first engagement mechanism may include a housing having an upper housing part and a lower housing part. The attachment mechanism and the locking mechanism may be arranged inside the housing, wherein the locking mechanism may be arranged on an inside of the upper housing part and on an inside of the lower housing part, and the attachment mechanism may be arranged on the inside of the lower housing part.

The first engagement mechanism may include a user grip or touch point (e.g., for lifting the table attach support and/or medical device) arranged on an outside of an underside of the lower housing part.

The first engagement mechanism may include a housing in which the attachment mechanism and the locking mechanism are arranged, and the medical device may further include a first user grip or touch point (e.g., for lifting the table attach support and/or medical device) arranged on an outside of an underside of the housing.

The positioning system may include a plurality of arms and rotational joints for positioning the robotic drive. The first of the plurality of arms may have a first end coupled to a top portion of the table attach support. The first of the plurality of arms may include a second user grip or touch point (e.g., for lifting the table attach support and/or medical device).

BRIEF DESCRIPTION OF THE DRAWINGS

Example embodiments will become more fully understood from the following detailed description, taken in conjunction with the accompanying drawings, wherein the reference numerals refer to like parts in which:

FIG. 3 is a side view of the catheter-based procedure system shown in FIG. 1 with certain components removed for clarity;

FIG. 9A illustrates a lock hook engaged with a crank in the locked position according to example embodiments.

FIG. 9B illustrates a rocker mount according to example embodiments.

FIG. 9C illustrates a lock hook according to example embodiments.

FIG. 9D illustrates a crank according to example embodiments.

FIG. 9E illustrates a lock linkage according to example embodiments.

FIG. 9F illustrates a button assembly secured to a rail clamp body according to example embodiments.

FIG. 9G is a cross-sectional view of the button assembly shown in FIG. 9F.

FIG. 11A is a top plan view of a portion of a table attach support according to other example embodiments.

FIG. 11B is a rear perspective view of a portion of the table attach support shown in FIG. 11A.

DETAILED DESCRIPTION

Figure 1:
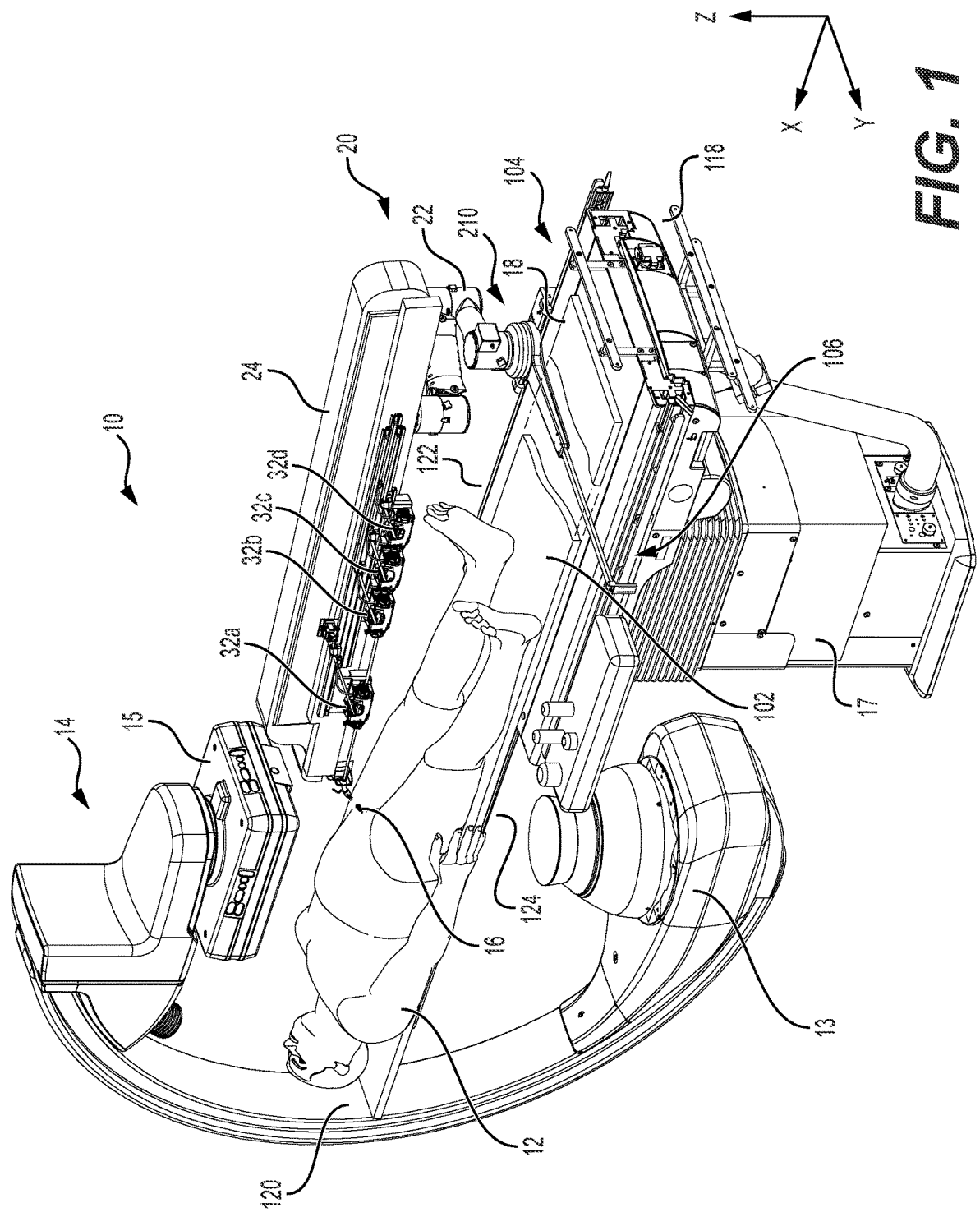
FIG. 1 is a perspective view of a catheter-based procedure system in accordance with example embodiments.

Various example embodiments will now be described more fully with reference to the accompanying drawings in which some example embodiments are shown.

Detailed illustrative embodiments are disclosed herein. However, specific structural and functional details disclosed herein are merely representative for purposes of describing example embodiments. The example embodiments may, however, be embodied in many alternate forms and should not be construed as limited to only the embodiments set forth herein.

It should be understood that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

As discussed herein the terminology "one or more" and "at least one" may be used interchangeably.

It will be appreciated that a number of example embodiments may be used in combination.

For clarity, elements and/or labels of elements shown in one figure may be omitted in other figures so as not to unnecessarily obscure certain other elements.

One or more example embodiments provide a table attach support having a locking mechanism that suppresses and/or prevents accidental release of the table attach support when attached to a patient table. One or more example embodiments also provide a positioning system including the table attach support and/or a medical device or system (e.g., a catheter-based procedure system) including the positioning system and/or table attach support. The table attach support may be used to secure the positioning system and/or medical device to a patient table for performing a medical procedure (e.g., a catheterization or other medical procedure) on a patient.

According to at least some example embodiments, to detach from (or, alternatively, attach to) the patient table, the table attach support may utilize a two-step process in which a user first releases a lever or handle (e.g., by pressing a lock release button on the rear of the table attach housing) to enable movement of the handle, and then pulls and/or rotates the handle to release (or, alternatively, secure) the table attach support from (or to) the table. According to at least some example embodiments, the lock release button may not eject the handle to the user in the event the button was pressed accidentally or unknowingly. Additionally, the handle may be positioned to overlap a hand pocket to indicate to the user that the handle should be moved before attempting to lift and/or move the positioning system and/or medical device or system.

One or more example embodiments also provide a positioning system having ergonomic and/or balanced touchpoints to enable a user to lift and place the system directly on the patient table and then remove the system from the patient table. The touchpoints may be designed such that hands of a user are away from pinch zones and do not require a change in grip when being secured and/or removed. One or more example embodiments also provide a catheter-based procedure system or other medical device including the positioning system.

FIG. 1 is a perspective view of catheter-based procedure system 10 in accordance with an example embodiment. The catheter-based procedure system 10 may be used to perform catheter-based medical procedures including percutaneous intervention procedures such as those discussed above, diagnostic catheterization procedures during which one or more catheters or other elongated medical devices (EMDs) are used to aid in the diagnosis of a patient's disease, catheter-based therapeutic procedures (e.g., angioplasty, stent placement, treatment of peripheral vascular disease, clot removal, arterial venous malformation therapy, treatment of aneurysm, etc.) during which a catheter (or other EMD) is used to treat a disease, or the like. The catheter-based procedure system 10 may perform any number of catheter-based medical procedures with minor adjustments to accommodate the specific percutaneous intervention devices to be used in the procedure.

The catheter-based procedure system 10 includes, among other elements, a bedside unit 20 and a control station (not shown). Bedside unit 20 includes a robotic drive 24 and a positioning system 22 that are located adjacent to a patient 12. Patient 12 is supported on a patient table 18. The positioning system 22 includes, among other things, a table attach support 210. The positioning system 22 is used to position and support the robotic drive 24. The positioning system 22 may be, for example, a robotic arm, an articulated arm, a holder, etc. The positioning system 22 is attached to the patient table 18 via a table attach support 210.

The patient table 18 includes a patient supporting surface 102 having a first longitudinal end 118, an opposing second longitudinal end 120, a first longitudinal side 122 and a second longitudinal side 124. First rail 104 extends from an outer periphery of the first longitudinal side 122 away from the second longitudinal side 124. Second rail 106 extends from an outer periphery of the second longitudinal side 124 in a direction away from first longitudinal side 122.

The robotic drive 24 is arranged on the positioning system 22. The positioning system 22 may be moved out of the way (along with the robotic drive 24) to allow for the patient 12 to be placed on the patient table 18. Once the patient 12 is positioned on the patient table 18, the positioning system 22 may be used to situate or position the robotic drive 24 relative to the patient 12 for the procedure. In at least one example embodiment, the patient table 18 is operably supported by a pedestal 17, which is secured to the floor and/or earth. The patient table 18 is configured to move with multiple degrees of freedom (e.g., roll, pitch, and yaw) relative to the pedestal 17. Bedside unit 20 may also include controls and displays 46 (shown in FIG. 2). For example, controls and displays may be located on a housing of the robotic drive 24.

The robotic drive 24 may be equipped with the appropriate percutaneous interventional devices and accessories 48 (shown in FIG. 2) (e.g., guidewires, various types of catheters including balloon catheters, stent delivery systems, stent retrievers, embolization coils, liquid embolics, aspiration pumps, device to deliver contrast media, medicine, hemostasis valve adapters, syringes, stopcocks, inflation device, etc.) to allow a user or operator to perform a catheter-based medical procedure via the robotic system by operating various controls such as the controls and inputs located at the control station. Bedside unit 20, and in particular robotic drive 24, may include any number and/or combination of components to provide bedside unit 20 with the functionality described herein.

The robotic drive 24 includes a plurality of device modules 32a, 32b, 32c, 32d mounted to a rail or linear member. Each of the device modules 32a-32d may be used to drive an EMD such as a catheter or guidewire. For example, the robotic drive 24 may be used to automatically feed a guidewire into a diagnostic catheter and into a guide catheter in an artery of the patient 12. One or more devices, such as an EMD, enter the body (e.g., a vessel) of the patient 12 at an insertion point 16 via, for example, an introducer sheath.

Bedside unit 20 is in communication with a control station (not shown), allowing signals generated by user inputs at the control station to be transmitted wirelessly or via hardwire to the bedside unit 20 to control various functions of bedside unit 20. As discussed below, the control station may include a control computing system 34 (shown in FIG. 2) or be coupled to the bedside unit 20 through the control computing system 34. Bedside unit 20 may also provide feedback signals (e.g., loads, speeds, operating conditions, warning signals, error codes, etc.) to the control station, control computing system 34 (shown in FIG. 2), or both. Communication between the control computing system 34 and various components of the catheter-based procedure system 10 may be provided via a communication link that may be a wireless connection, cable connections, or any other means capable of allowing communication to occur between components. The control station or other similar control system may be located either at a local site (e.g., local control station 38 shown in FIG. 2) or at a remote site (e.g., remote control station and computing system 42 shown in FIG. 2). Catheter-based procedure system 10 may be operated by a control station at the local site, a control station at a remote site, or both the local control station and the remote control station at the same time. At a local site, a user or operator and the control station may be located in the same room or an adjacent room to the patient 12 and bedside unit 20. As used herein, a local site is the location of the bedside unit 20 and the patient 12 or subject (e.g., animal or cadaver), whereas the remote site is the location of a user or operator and a control station used to control the bedside unit 20 remotely. A control station (and a control computing system) at a remote site and the bedside unit 20 and/or a control computing system at a local site may be in communication using communication systems and services 36 (shown in FIG. 2), for example, through the Internet.

The control station generally includes one or more input modules 28 configured to receive user inputs to operate various components or systems of catheter-based procedure system 10. In the example embodiment shown, the control station allows the user or operator to control the bedside unit 20 to perform a catheter-based medical procedure. For example, input modules 28 (shown in FIG. 2) may be configured to cause bedside unit 20 to perform various tasks using percutaneous intervention devices (e.g., EMDs) interfaced with the robotic drive 24 (e.g., to advance, retract, or rotate a guidewire, advance, retract or rotate a catheter, inflate or deflate a balloon located on a catheter, position and/or deploy a stent, position and/or deploy a stent retriever, position and/or deploy a coil, inject contrast media into a catheter, inject liquid embolics into a catheter, inject medicine or saline into a catheter, aspirate on a catheter, or to perform any other function that may be performed as part of a catheter-based medical procedure). Robotic drive 24 includes various drive mechanisms to cause movement (e.g., axial and rotational movement) of the components of the bedside unit 20 including the percutaneous intervention devices.

In an example embodiment, input modules 28 may include one or more touch screens, joysticks, scroll wheels, and/or buttons. In addition to input modules 28, the control station may use additional user controls 44 (shown in FIG. 2) such as foot switches and microphones for voice commands, etc. Input modules 28 may be configured to advance, retract, or rotate various components and percutaneous intervention devices such as, for example, a guidewire, and one or more catheters or microcatheters. Buttons may include, for example, an emergency stop button, a multiplier button, device selection buttons and automated move buttons. In an example embodiment, input modules 28 may include one or more controls or icons (not shown) displayed on a touch screen (that may or may not be part of a display), that, when activated, cause operation of a component of the catheter-based procedure system 10. Input modules 28 may also include a balloon or stent control that is configured to inflate or deflate a balloon and/or deploy a stent. Each of the input modules 28 may include one or more buttons, scroll wheels, joysticks, touch screen, etc. that may be used to control the particular component or components to which the control is dedicated. In addition, one or more touch screens may display one or more icons (not shown) related to various portions of input modules 28 or to various components of catheter-based procedure system 10.

Still referring to FIG. 1, catheter-based procedure system 10 also includes an imaging system 14. Imaging system 14 may be any medical imaging system that may be used in conjunction with a catheter-based medical procedure (e.g., non-digital X-ray, digital X-ray, CT, MRI, ultrasound, etc.). In an example embodiment, the imaging system 14 is a digital X-ray imaging device that is in communication with the control station. The imaging system 14 may include a C-arm 120 that allows the imaging system 14 to partially or completely rotate around the patient 12 to obtain images at different angular positions relative to the patient 12 (e.g., sagittal views, caudal views, anterior-posterior views, etc.). In at least one example, the imaging system 14 is a fluoroscopy system including a C-arm having an X-ray source 13 and a detector 15, also known as an image intensifier.

The imaging system 14 may be configured to take X-ray images of the appropriate area of the patient 12 during a procedure. For example, imaging system 14 may be configured to take one or more X-ray images of the head to diagnose a neurovascular condition. Imaging system 14 may also be configured to take one or more X-ray images (e.g., real time images) during a catheter-based medical procedure to assist the user or operator 11 of a control station to properly position a guidewire, guide catheter, microcatheter, stent retriever, coil, stent, balloon, etc. during the procedure. The image or images may be displayed on display 30. For example, images may be displayed on a display to allow the user or operator to accurately move a guide catheter or guidewire into the proper position.

Figure 2:
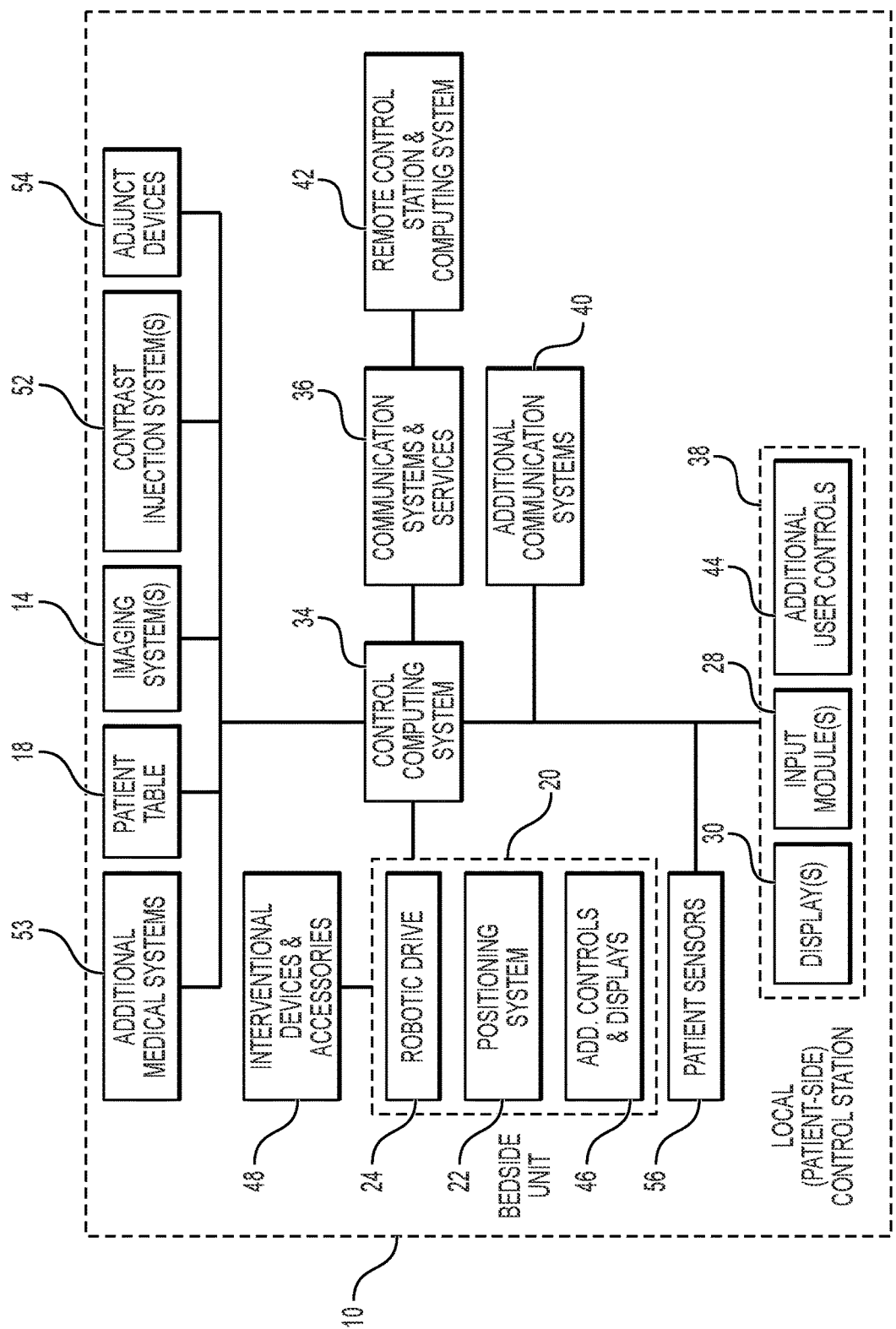
FIG. 2 is a schematic block diagram of a catheter-based procedure system in accordance with example embodiments.

FIG. 2 is a block diagram of catheter-based procedure system 10 in accordance with an example embodiment. Catheter-based procedure system 10 may include a control computing system 34. Control computing system 34 may physically be, for example, part of the control station. Control computing system 34 may generally be an electronic control unit suitable to provide catheter-based procedure system 10 with the various functionalities described herein. For example, control computing system 34 may be an embedded system, a dedicated circuit, a general-purpose system programmed with the functionality described herein, etc. Control computing system 34 is in communication with bedside unit 20, communications systems and services 36 (e.g., Internet, firewalls, cloud services, session managers, a hospital network, etc.), a local control station 38, additional communications systems 40 (e.g., a telepresence system), a remote control station and computing system 42, and patient sensors 56 (e.g., electrocardiogram (ECG) devices, electroencephalogram (EEG) devices, blood pressure monitors, temperature monitors, heart rate monitors, respiratory monitors, etc.). The control computing system 34 is also in communication with imaging system 14, patient table 18, additional medical systems 53, contrast injection systems 52 and adjunct devices 54 (e.g., IVUS, OCT, FFR, etc.). The bedside unit 20 includes robotic drive 24, positioning system 22 and may include additional controls and displays 46. As mentioned above, the additional controls and displays 46 may be located on a housing of the robotic drive 24. Interventional devices and accessories 48 (e.g., guidewires, catheters, etc.) interface with the bedside unit 20. In an example embodiment, interventional devices and accessories 48 may include specialized devices (e.g., IVUS catheter, OCT catheter, FFR wire, diagnostic catheter for contrast, etc.), which interface to their respective adjunct devices 54, namely, an IVUS system, an OCT system, and FFR system, etc.

In various example embodiments, control computing system 34 is configured to generate control signals based on the user's interaction with input modules 28 (e.g., of a control station such as a local control station 38 or a remote control station and computing system 42) and/or based on information accessible to control computing system 34 such that a medical procedure may be performed using catheter-based procedure system 10. The local control station 38 includes one or more displays 30, one or more input modules 28, and additional user controls 44. The remote control station and computing system 42 may include similar components to the local control station 38. The remote control station and computing system 42 and local control station 38 may be different and/or tailored based on their required functionalities. The additional user controls 44 may include, for example, one or more foot input controls. The foot input control may be configured to allow the user to select functions of the imaging system 14 such as turning on and off the X-ray and/or scrolling through different stored images. In another example embodiment, a foot input device may be configured to allow the user to select which devices are mapped to scroll wheels included in input modules 28. Additional communication systems 40 (e.g., audio conference, video conference, telepresence, etc.) may be employed to help the operator interact with the patient, medical staff (e.g., angio-suite staff), and/or equipment in the vicinity of the bedside.

Catheter-based procedure system 10 may be connected or configured to include any other systems and/or devices not explicitly shown. For example, catheter-based procedure system 10 may include image processing engines, data storage and archive systems, automatic balloon and/or stent inflation systems, medicine injection systems, medicine tracking and/or logging systems, user logs, encryption systems, systems to restrict access or use of catheter-based procedure system 10, etc.

FIG. 3 is a side view of the catheter-based procedure system 10 of FIG. 1 with certain components (e.g., patient, C-arm) removed for clarity. As described above with reference to FIG. 1, the patient table 18 is supported on the pedestal 17, and the robotic drive 24 is mounted to the patient table 18 with the positioning system 22 via the table attach support 210. The positioning system 22 allows manipulation of the robotic drive 24 relative to the patient table 18. In this regard, the positioning system 22 is securely mounted to the patient table 18 by the table attach support 210 and includes various joints and links/arms to allow the manipulation.

Figure 4A:
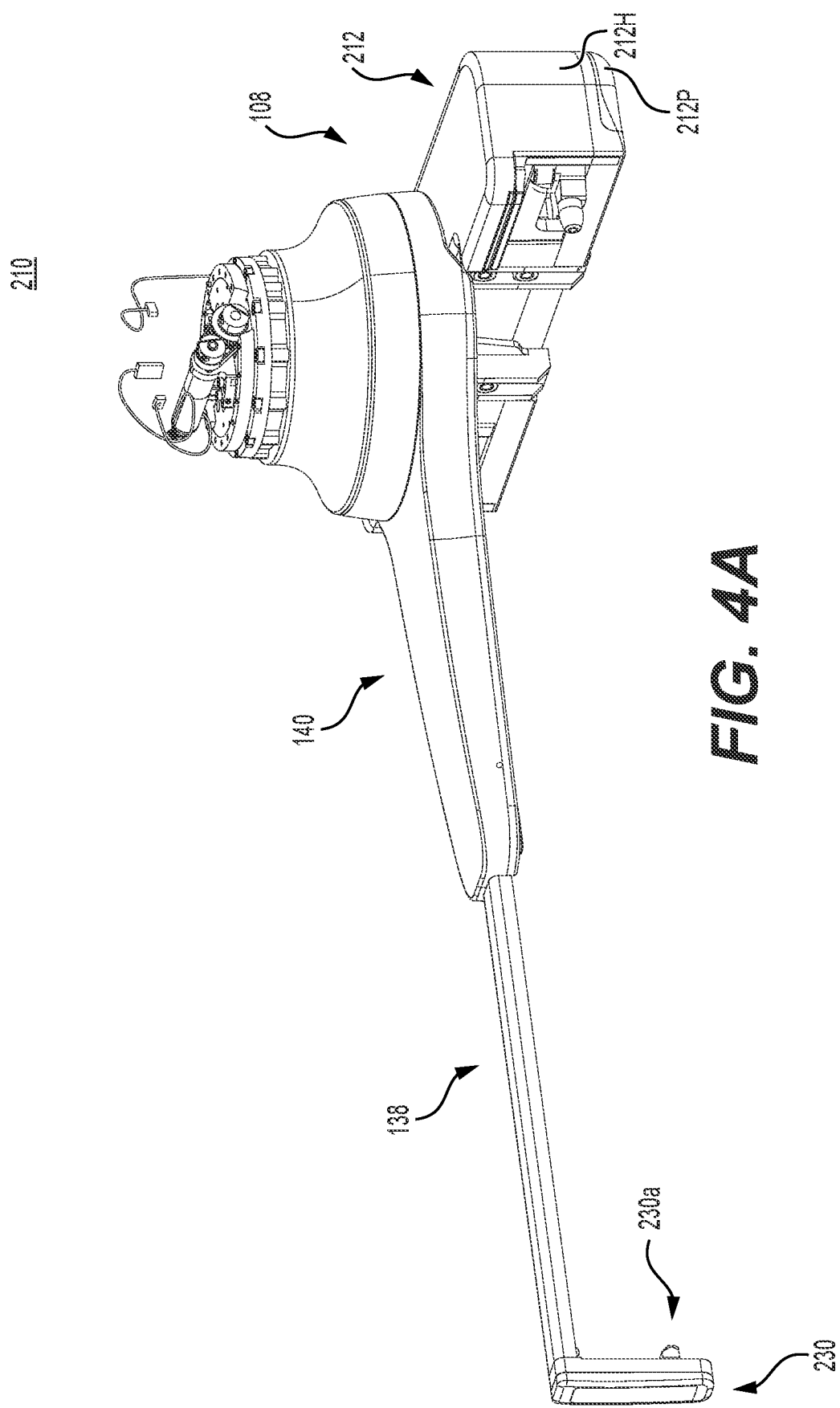
FIGS. 4A and 4B are perspective views of a table attach support for a robotic drive in accordance with example embodiments.
Figure 4B:
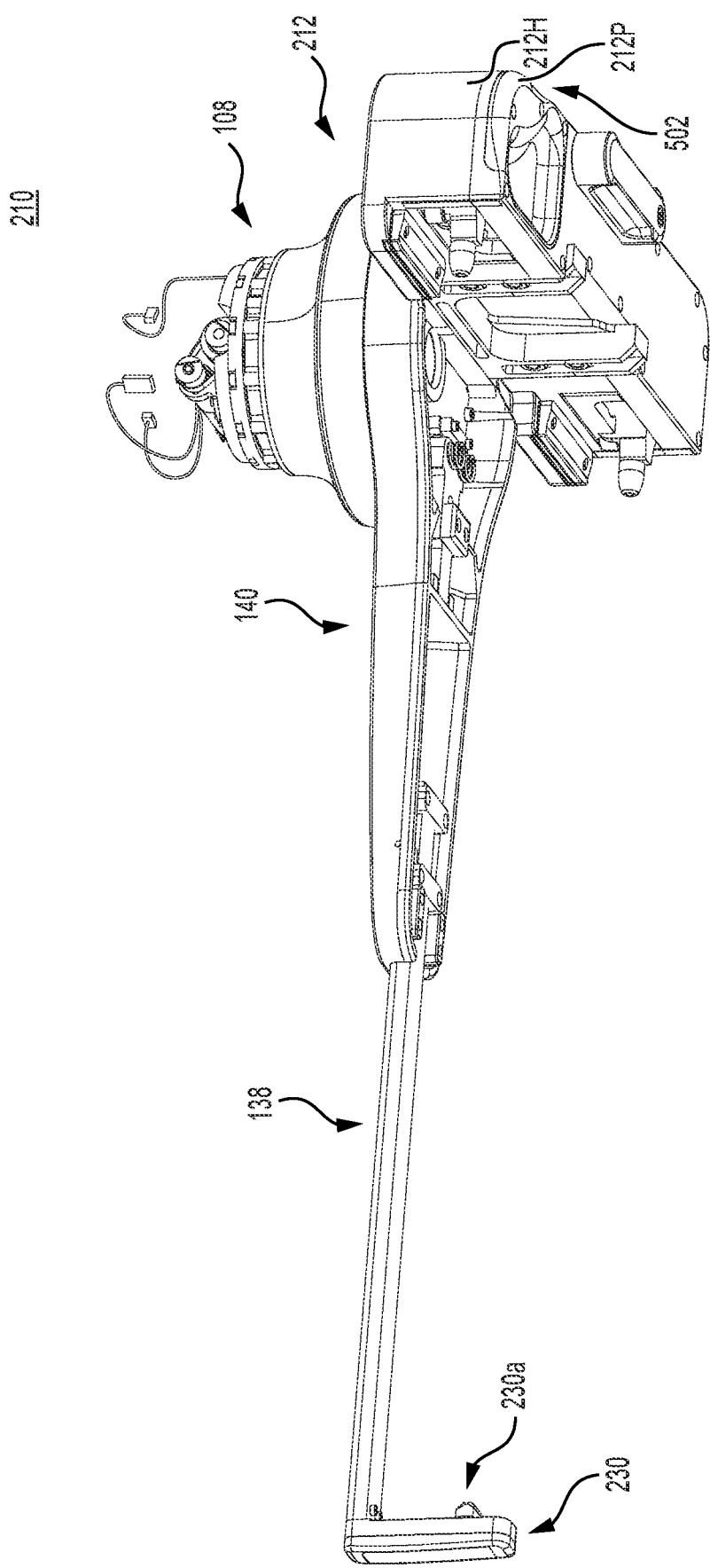
Figure 5A:
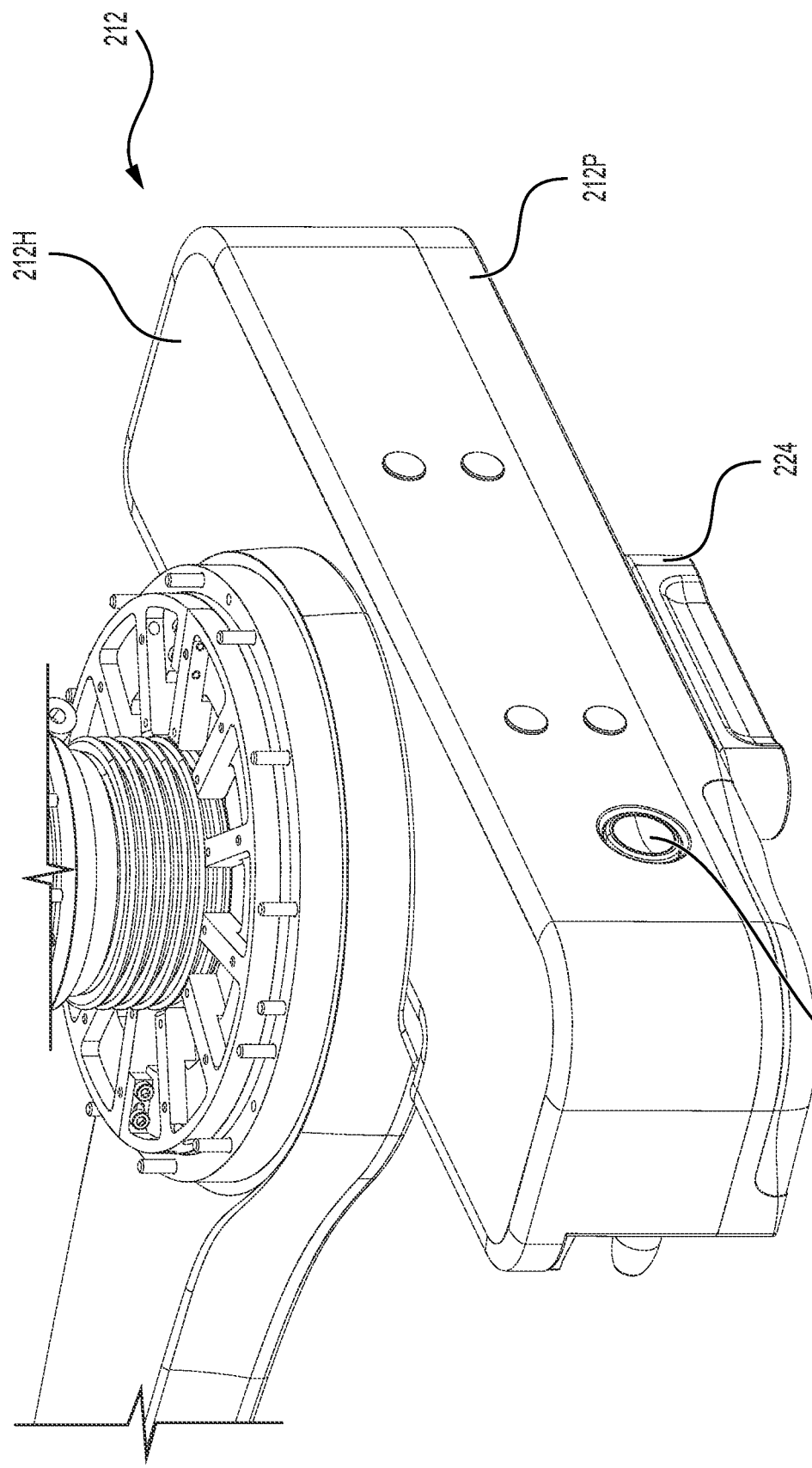
FIG. 5A is a perspective view of a portion of the table attach support shown in FIGS. 4A and 4B.
Figure 5B:
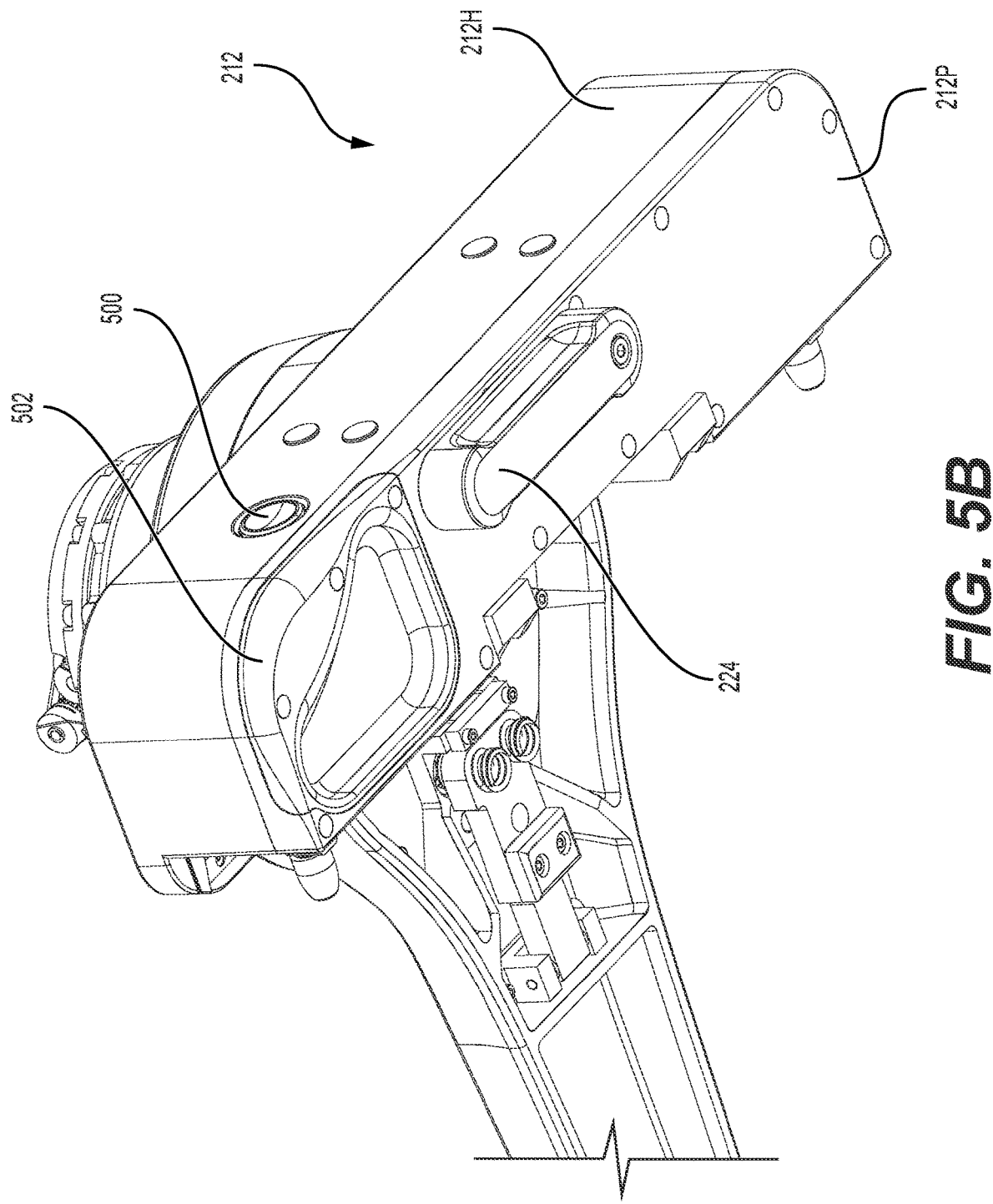
FIG. 5B is another perspective view of a portion of the table attach support shown in FIGS. 4A and 4B.
Figure 5C:
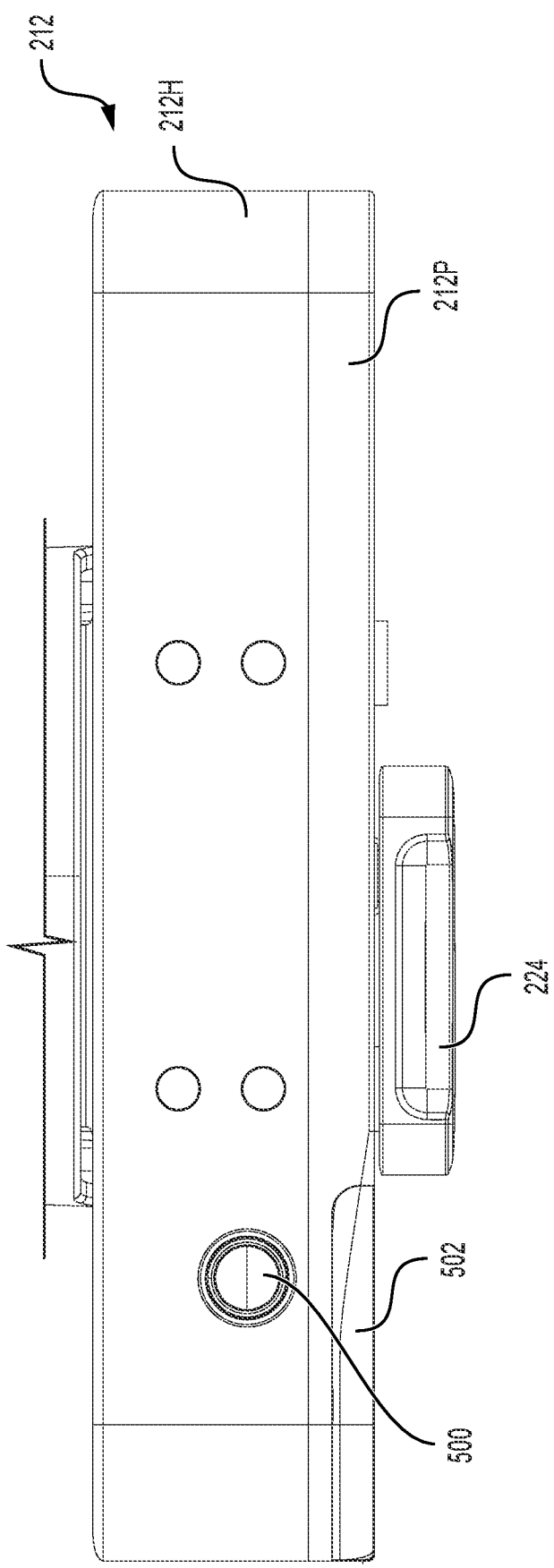
FIGS. 5C and 5D are rear elevation views of the table attach support shown in FIGS. 4A and 4B.
Figure 5D:
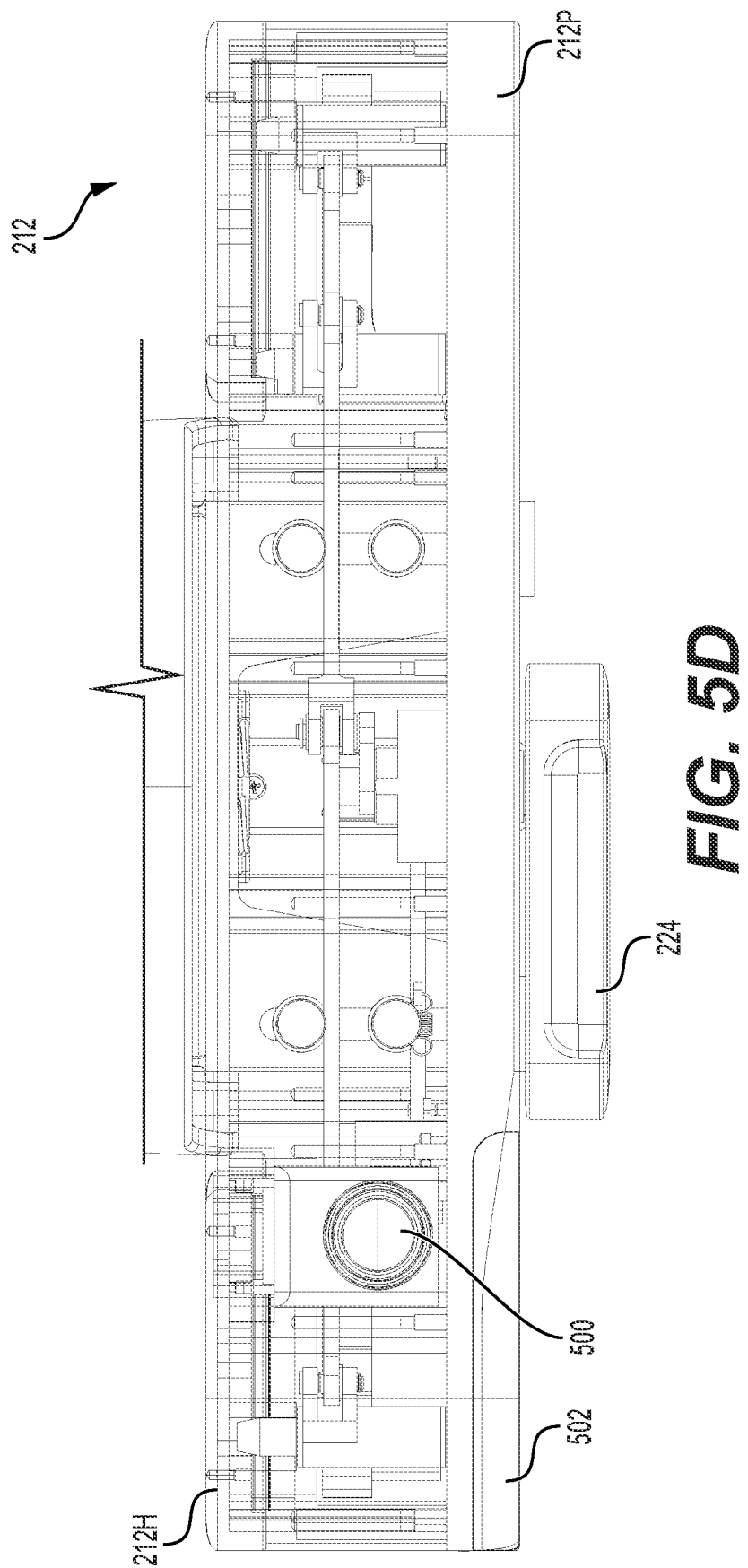

FIGS. 4A and 4B are perspective views of the table attach support 210 shown in FIGS. 1 and 3. FIGS. 5A-5D illustrate various views of a portion of the table attach support 210 shown in FIGS. 4A and 4B. In each of FIGS. 4A, 4B and 5A-5D, the table attach support 210 is in the engaged position. In FIG. 5D, a rail clamp body 212H is transparent so as to allow for view of some of the internal components of the table attach support 210.

As discussed herein, a side of the table attach support 210 facing the patient table 18 when attached is referred to as the table-side or front of the table attach support, whereas the opposite side is referred to as the rear or non-table-side of the table attach support. However, example embodiments should not be limited by this description.

Referring to FIGS. 4A-5D, the table attach support 210 includes a base 108 rotatably mounted on a body 140. Although not shown, additional components of the positioning system 22, discussed later with regard to FIG. 15, may be mounted on the base 108. The body 140 is fixed to, or integrated with, a first engagement mechanism 212. The table attach support 210 further includes a cross-arm 138 and a second engagement mechanism 230. The cross-arm 138 is configured to slidably extend from the body 140 and may be adjusted relative to the body 140 to accommodate patient tables having different cross-table dimensions. The second engagement mechanism 230 includes a tab 230a having an upper beveled surface that guides a lower surface of the opposing rail 106 of the patient table 18 to an upper planar surface of the tab 230a when attached to the patient table 18.

The first engagement mechanism 212 includes an outer housing comprising the rail clamp body 212H (also referred to as an upper housing or upper housing part) and a rail clamp plate 212P (also referred to as a lower housing or lower housing part) to which the rail clamp body 212H is fixed when assembled. In one example, the rail clamp body 212H is fixed to the rail clamp plate 212P via screws or other fixing devices inserted through screw or fixing holes at the bottom of the rail clamp plate 212P.

The table attach support 210 further includes a first grip 502 and a handle 224 on the underside of the rail clamp plate 212P. A button 500 (also referred to herein as a release button, a lock release button or a lock/unlock button) is arranged at a rear of the rail clamp body 212H.

As discussed in more detail later, the first engagement mechanism 212 includes linkages and mechanisms configured to enable a user to secure the table attach support 210 to the patient table 18 by moving the handle 224. The first engagement mechanism 212 and the second engagement mechanism 230 may physically engage and secure the table attach support 210 to the patient table 18 in the same or substantially the same manner as discussed in U.S. application Ser. No. 17/813,154, titled "Support for Securing a Robotic System to a Patient Table," the entire contents of which are incorporated herein by reference.

The first engagement mechanism 212 and components thereof will be discussed in more detail below.

Figure 6A:
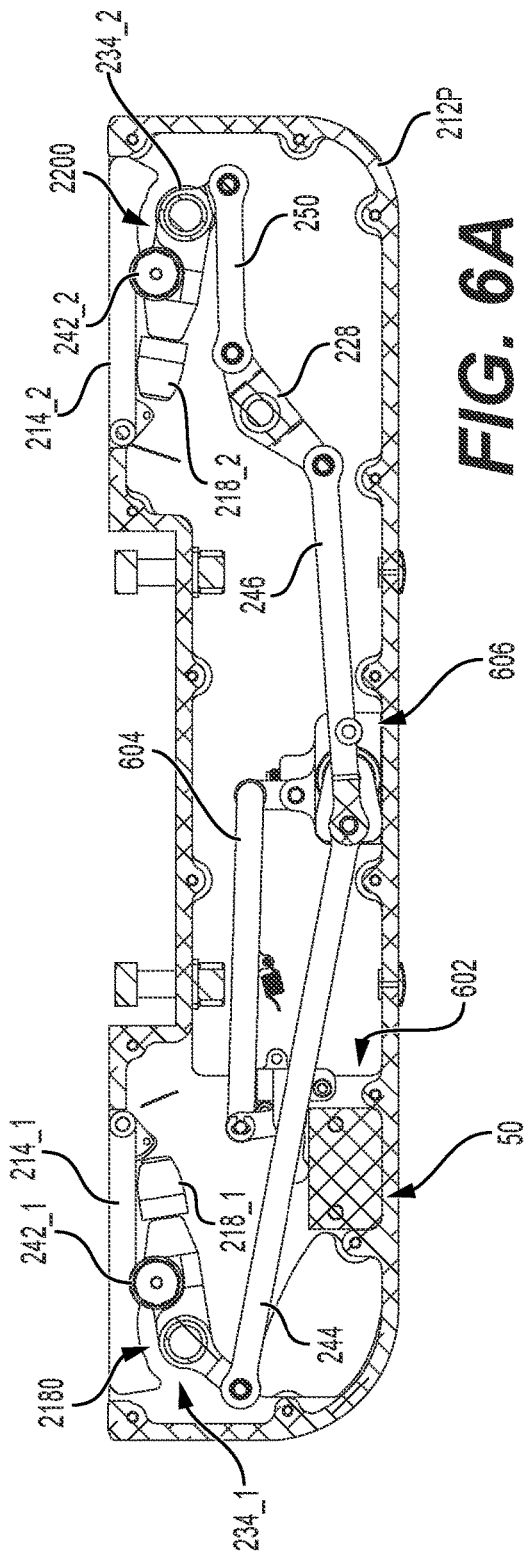
FIGS. 6A, 6B and 6C are top plan views of the table attach support shown in FIGS. 4A and 4B with the top portion of the rail clamp body removed.
Figure 6B:
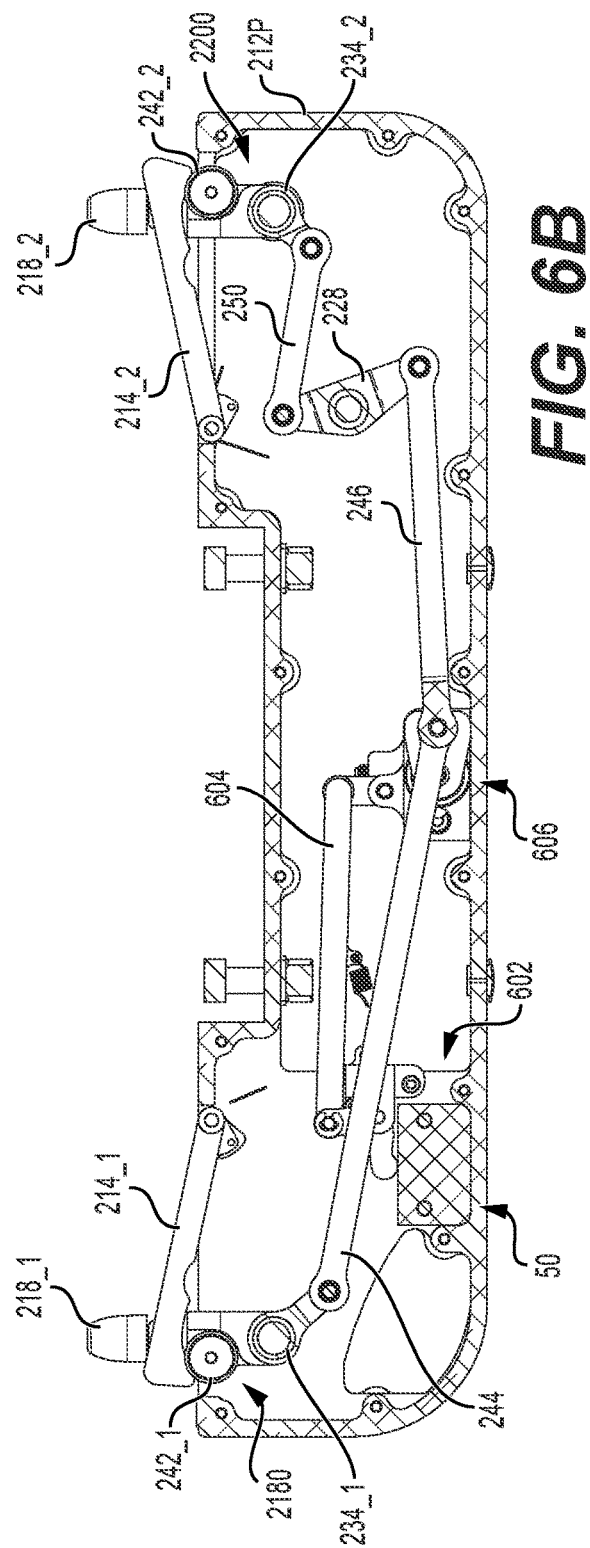
Figure 6C:
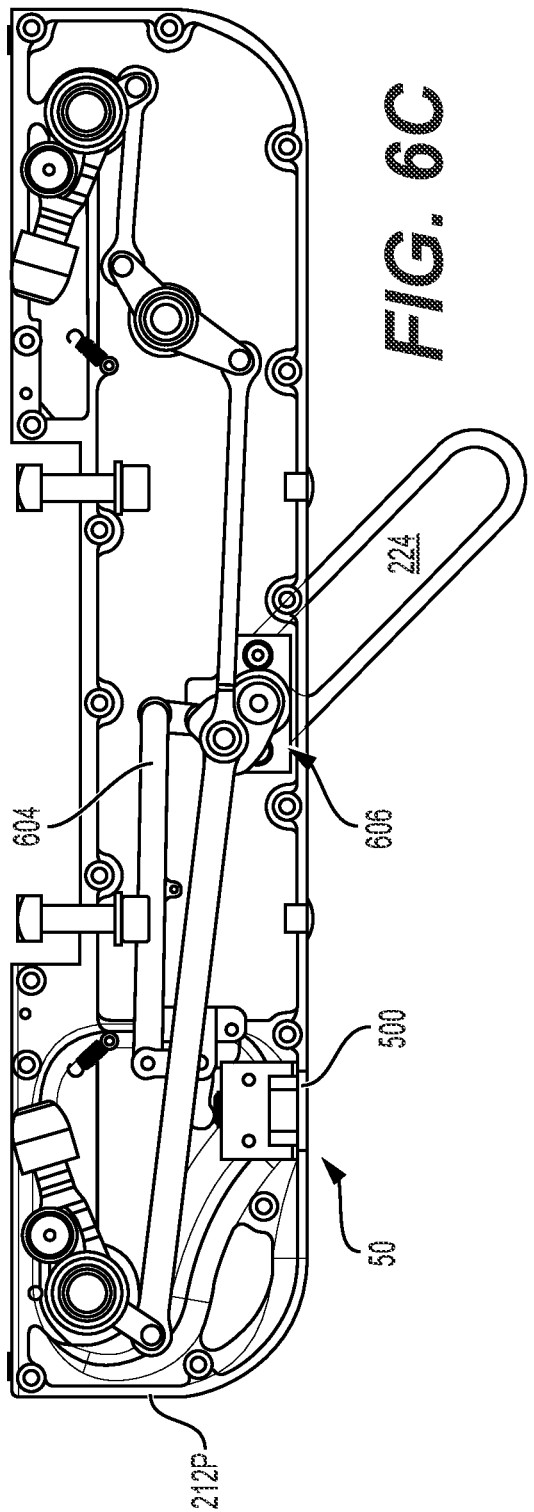

FIGS. 6A-6C are top plan views of the first engagement mechanism 212 shown in FIGS. 4A and 4B with the top portion of the rail clamp body 212H removed. In more detail, FIG. 6A illustrates the first engagement mechanism 212 in a disengaged position, FIG. 6B illustrates the first engagement mechanism 212 in an engaged position, and FIG. 6C illustrates the first engagement mechanism 212 being actuated from the disengaged position to the engaged position.

Figure 7:
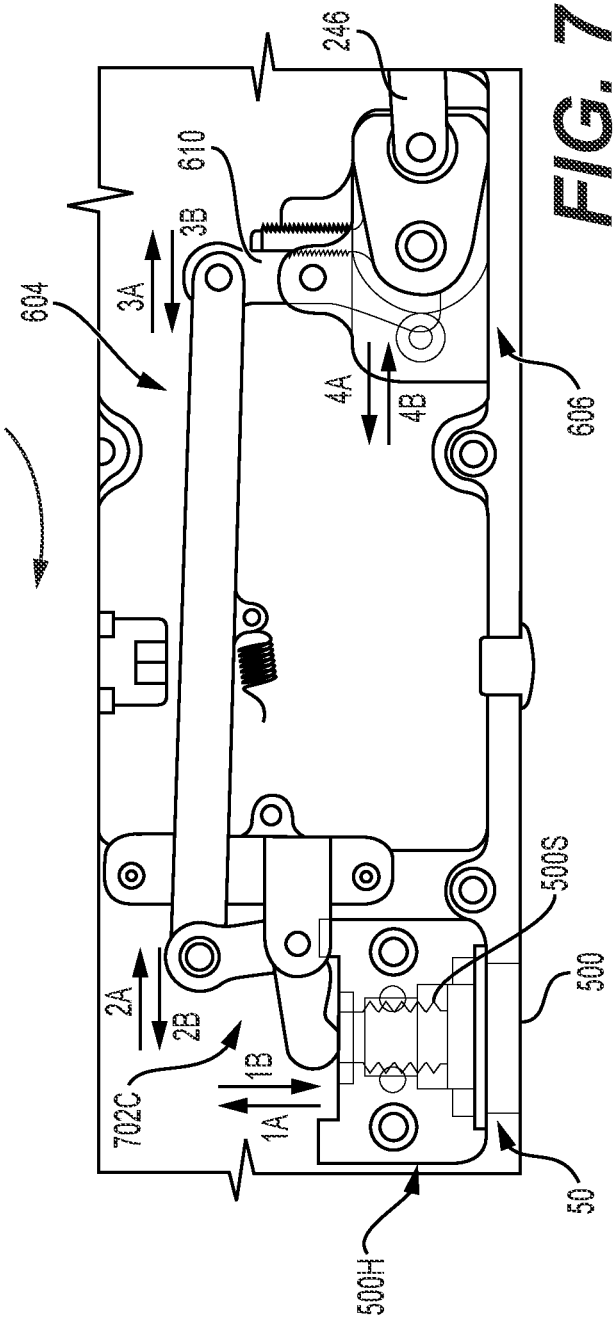
FIG. 7 is an enlarged view of a portion of a top plan view of the table attach support shown in FIGS. 4A and 4B.

FIG. 7 is an enlarged view of a portion of the top plan view of the first engagement mechanism 212 in the engaged position.

Figure 8A:
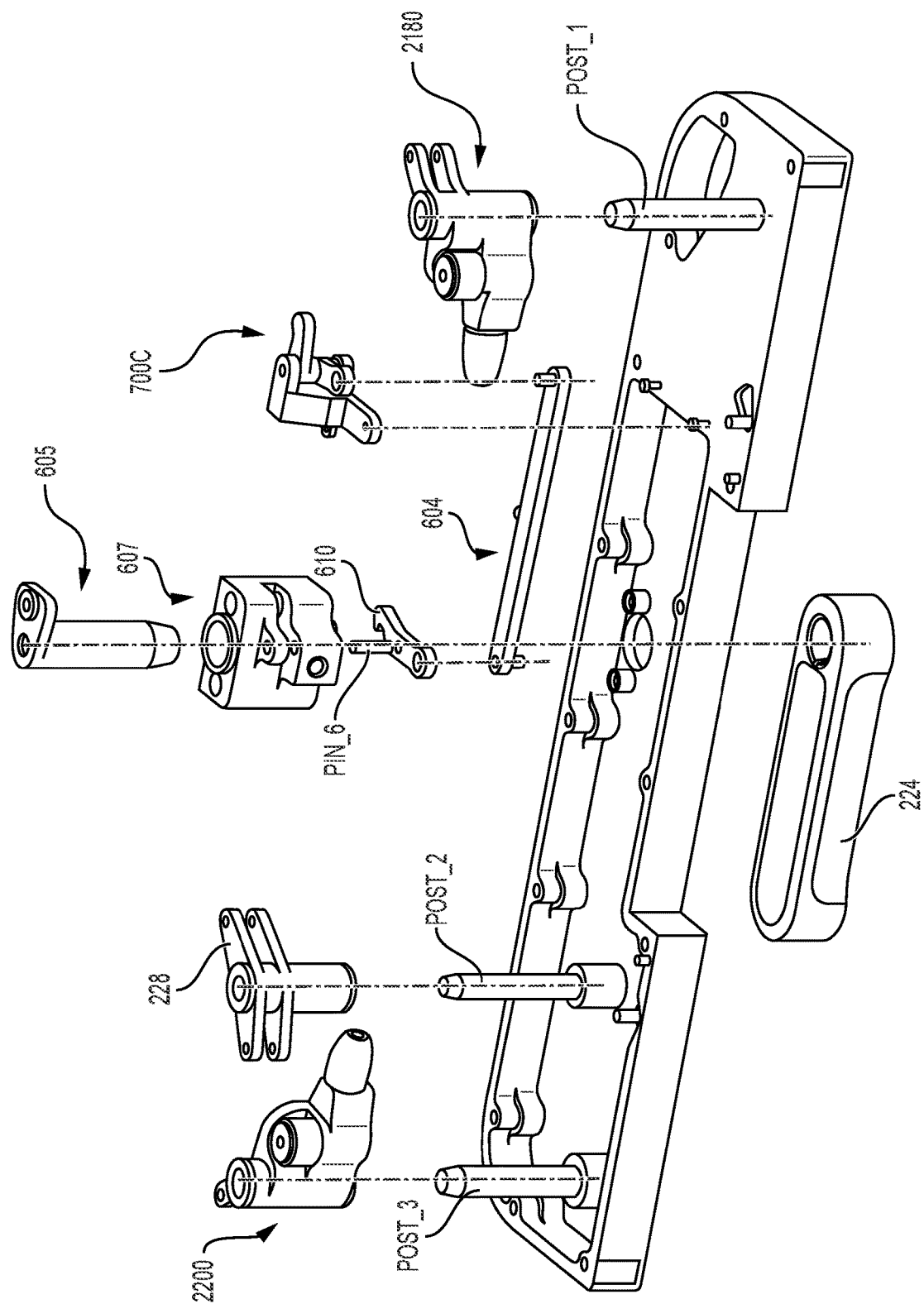
FIGS. 8A, 8B and 8C illustrate various stages of assembly of a rail clamp plate according to example embodiments.
Figure 8B:
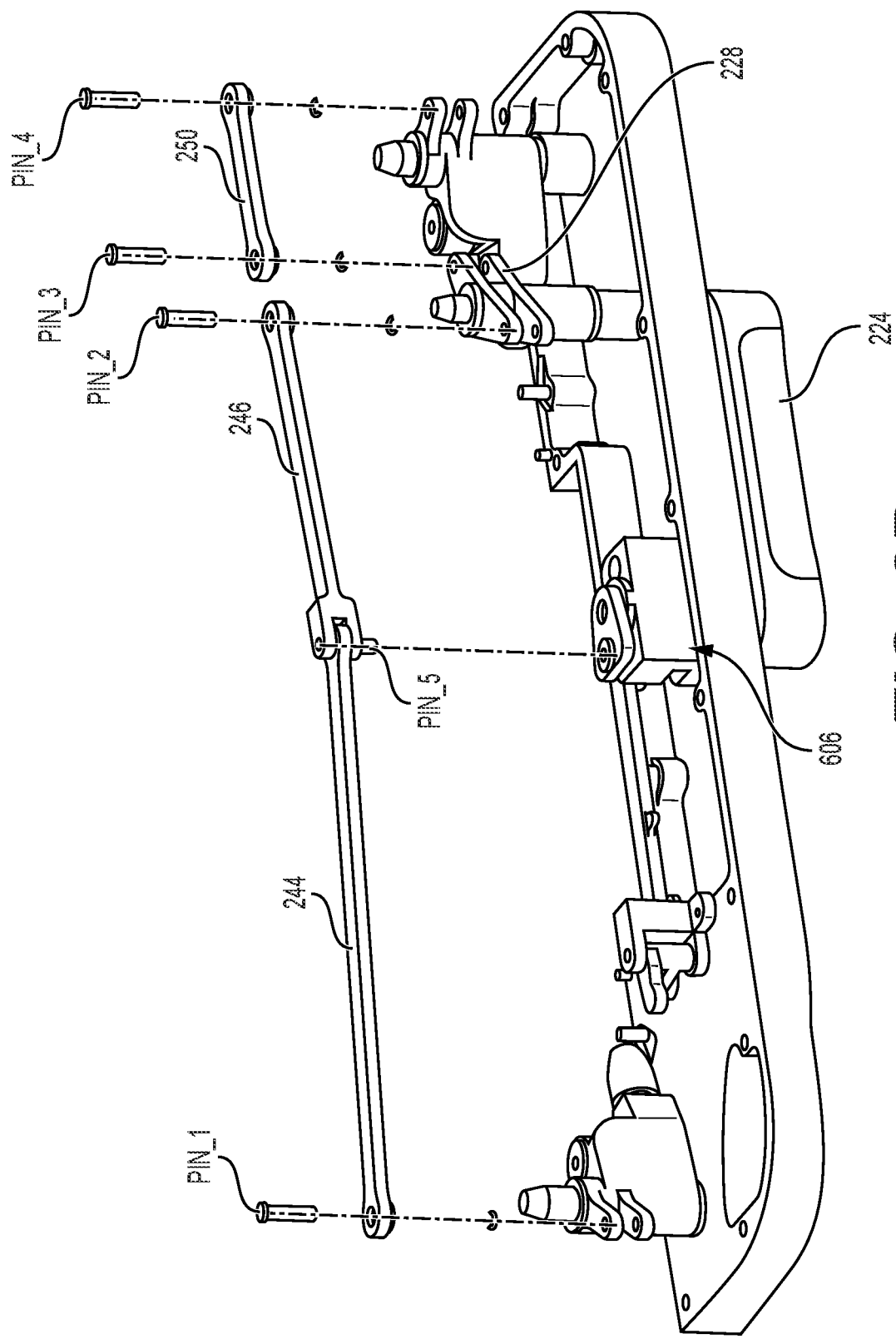
Figure 8C:
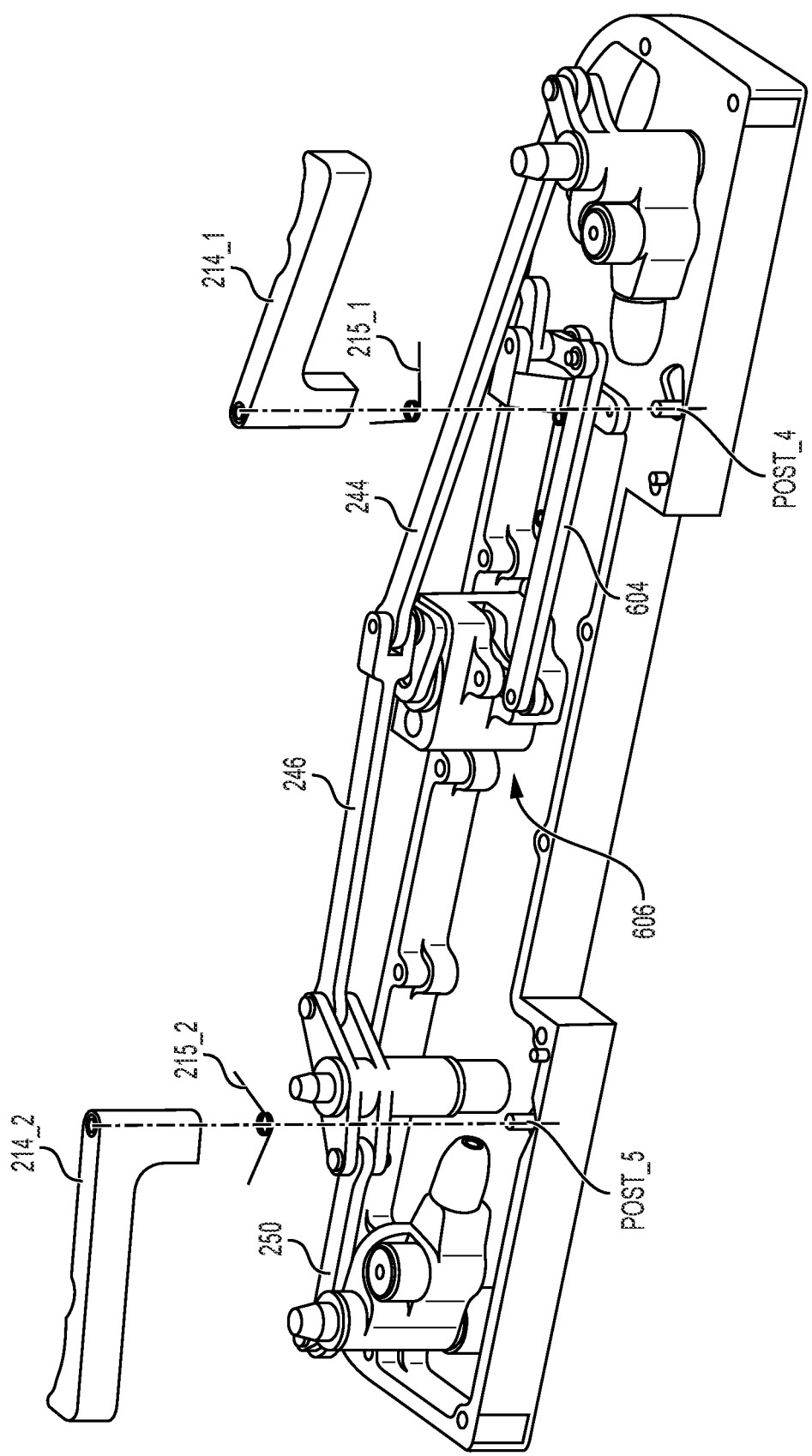

FIGS. 8A-8C illustrate various stages of assembly of the rail clamp plate 212P, according to example embodiments.

Referring to FIGS. 6A-7 and 8A-8C, a first roller cam assembly 2180 includes a first roller cam 218_1, a first guide roller 242_1 and a first member 234_1. The first roller cam 218_1 includes a first frustoconical portion and a second conical portion. The first roller cam assembly 2180 is fitted over, and configured to rotate about, a vertical post (or cam shaft) POST_1 extending vertically from the rail clamp plate 212P.

An end of the first roller cam assembly 2180 is pivotably engaged to a first end of first linkage 244 via a pin PIN_1. A second, opposite end of the first linkage 244 is pivotably engaged with a first end of a second linkage 246 via pin PIN_5. Pin PIN_5 also pivotably secures the first linkage 244 and the second linkage 246 to a crank lock assembly 606. The handle 224 is secured to the crank lock assembly 606 at the bottom of the rail clamp plate 212P. The crank lock assembly 606 and the handle 224 will be discussed in more detail later.

Still referring to FIGS. 6A-7 and 8A-8C, a reverse rocker 228 is fitted over, and configured to rotate about, a vertical post (or cam shaft) POST_2 extending vertically from the rail clamp plate 212P. A second end of the second linkage 246 is pivotably engaged with an end of the reverse rocker 228 via pin PIN_2. A first end of a third linkage 250 is pivotably engaged with a second end of the reverse rocker 228 via pin PIN_3. A second, opposite end of the third linkage 250 is pivotably engaged with an end of the second roller cam assembly 2200 via pin PIN_4.

The second roller cam assembly 2200 includes a second roller cam 218_2, a second guide roller 242_2 and a second member 234_2. The second roller cam assembly 2200 is fitted over, and configured to rotate about, a vertical post (or cam shaft) POST_3 extending vertically from the rail clamp plate 212P. Similar to the first roller cam 218_1, the second roller cam 218_2 includes a first frustoconical portion and a second conical portion. The reverse rocker 228 enables the first roller cam assembly 2180 and the second roller cam assembly 2200 to rotate in opposite directions when actuated by moving the handle 224.

First and second paddles 214_1 and 214_2 are pivotably engaged with the rail clamp plate 212P via respective paddle posts POST_4 and POST_5 so as to rotate about the respective paddle posts as a result of force applied by the respective roller cam assemblies 2180 and 2200 when securing the table attach support 210 to the patient table 18. The first paddle 214_1 is spring biased against the first guide roller 242_1 by a biasing member 215_1 (e.g., a spring). Similarly, the second paddle 214_2 is spring biased against second guide roller 242_2 by a biasing member 215_2 (e.g., a spring).

In the disengaged position, the first paddle 214_1, the first roller cam assembly 2180, the second paddle 214_2, and the second roller cam assembly 2200 are in a first, retracted position as shown in FIG. 6A, for example. In this example, the roller cam assemblies 2180 and 2200 are withdrawn into or substantially into the housing of the first engagement mechanism 212.

As described herein, one or more of the roller cam assemblies 2180 and 2200, paddles 214_1 and 214_2, and the associated linkages and mechanisms may be collectively referred to as an attachment mechanism. The linkages operatively coupling the first roller cam assembly 2180 with the second roller cam assembly 2200 may be collectively referred to as a linkage assembly.

Still referring to FIGS. 6A-7 and 8A-8C, the rail clamp plate 212P further includes a locking mechanism configured to suppress and/or prevent accidental release of the table attach support 210 when in the engaged position and/or secured to the patient table 18. In some example embodiments, the locking mechanism may also suppress and/or prevent unintended movement of the handle 224 when attaching the table attach support 210 to the patient table 18. As discussed in more detail below, the locking mechanism may utilize a two-step process to enable movement of the handle 224 to release the table attach support 210 from engagement with the patient table 18. In one example, the user first releases a handle 224 (e.g., by pressing the button 500) to enable movement of the handle 224. Once released, the user is able to rotate the handle 224 (e.g., counterclockwise) to move the first engagement mechanism 212 to the disengaged position and release the table attach support 210 from the patient table 18.

According to at least some example embodiments, the button 500 does not eject the handle 224, in the event the button 500 was pressed accidentally or unknowingly. The user pushes the button 500 and concurrently and/or simultaneously pulls or rotates the handle 224 to release the table attach support 210.

According to one or more example embodiments, the locking mechanism includes a button assembly 50 (also referred to as lock release button assembly), the crank lock assembly 606 and a lock linkage 604.

The crank lock assembly 606 includes a crank 605, a body member 607, a lock hook 610 and a pin PIN_6. An example embodiment of the lock hook 610 is shown in FIG. 9C and an example embodiment of the crank 605 is shown in FIG. 9D.

Referring to FIG. 9D, the crank 605 includes a longitudinal shaft portion 700D with a flat flange portion 706D at a first end and a tapered second end opposite the first end. Although not shown, at least a portion of the bottom of the longitudinal shaft portion 700D may be hollow and threaded to accommodate a screw or other fixing device to rotatably secure the handle 224 to the rail clamp plate 212P when assembled. A pin PIN_7 extends vertically from the flat flange portion 706D in parallel with the longitudinal axis of the crank 605. The longitudinal shaft portion 700D includes at least one notch 702D. Although only one notch is shown in FIG. 9D, a second notch may be arranged opposite the first notch 702.

Referring to FIG. 9C, the lock hook 610 includes a hook portion 700F and a plurality of through pinholes 710C to accommodate assembly pins. The lock hook 610 will be discussed in more detail later.

Returning to FIGS. 6A-7 and 8A-8C, the body member 607 is secured to the rail clamp plate 212P. As shown in FIG. 8A (and FIG. 9A), for example, the body member 607 has a cylindrical hole in which the longitudinal shaft portion 700D of the crank 605 is arranged. The body member 607 also includes a horizontal slot at a middle portion thereof to accommodate the lock hook 610. The lock hook 610 is inserted and secured in the slot via the pin PIN_6 inserted through one of the pinholes 710C in the lock hook 610 and a pinhole in the body member 607. The lock hook 610 is configured to pivot about the pin PIN_6 in response to force exerted by the lock linkage 604 during actuation (e.g., pressing) of the button 500.

The longitudinal shaft portion 700D passes through the hole in the body member 607 and through a bottom hole in the rail clamp plate 212P. The handle 224 is secured to the tapered end of the crank 605 (e.g., via a screw inserted into the bottom of the longitudinal shaft portion 700D) such that rotation of the handle 224 translates into rotation of the crank 605 in the same direction (e.g., clockwise or counterclockwise).

FIG. 9A is a horizontal cross-section of the crank lock assembly 606 illustrating the lock hook 610 engaged with the crank 605 in the locked position. As shown, when in the locked position, the hook portion 700F is positioned in the notch 702D to prevent rotation of the crank 605 and the handle 224. According to one or more example embodiments, the hook portion 700F may engage with the notch 702D when the first engagement mechanism 212 is in the fully engaged position. As mentioned above, although not shown in FIG. 9A, the longitudinal shaft portion 700D may have a second notch opposite the first notch to prevent movement of the handle 224 when in the disengaged position.

The lock linkage 604 operatively connects the lock hook 610 and a rocker mount 700C of the button assembly 50.

FIG. 9E illustrates an example embodiment of the lock linkage 604 isolated from other elements of the rail clamp plate 212P.

As shown in FIGS. 8A and 9E, for example, the lock linkage 604 includes pin portions 700E and 702E at respective ends thereof and a longitudinal body portion 704E extending between the respective ends. The pin portions 700E and 702E extend perpendicular to the longitudinal axis of the longitudinal body portion 704E and in opposite directions relative to one another. A spring attachment member 706E is arranged at a middle portion of the longitudinal body portion 704E for attaching a biasing member, such as a spring (not shown).

Returning again to FIGS. 6A-7 and 8A-8C, the pin portion 702E is inserted into the pinhole 710C of the lock hook 610 and the pin portion 700E is inserted into a pinhole 706C in the rocker mount 700C. As discussed in more detail later, force exerted on the lock linkage 604 causes the lock hook 610 to rotate about the pin PIN_6 to disengage from the notch 702D and allow movement of the handle 224.

As discussed in more detail later, the button assembly 50 includes the button 500 and the rocker mount 700C. The button assembly 50 is configured to allow movement of the handle 224 and the first engagement mechanism 212 from the fully engaged position to the fully disengaged position, or vice versa, when pressed by a user. The button 500 is spring biased towards the rear of the first engagement mechanism 212 such that the button 500 returns to the initial position flush or substantially flush with the outer housing once released by the user.

The rocker mount 700C is fixed to the rail clamp plate 212P. FIG. 9B illustrates an example embodiment of the rocker mount 700C in more detail.

Referring to FIG. 9B, the rocker mount 700C includes a movable member 702C and a stationary member 704C. The movable member 702C includes a pinhole 706C and a button engagement portion 708C.

The movable member 702C is pivotably secured to the stationary member 704C via a pin PIN_8 such that the movable member 702C is configured to rotate or pivot about the pin PIN_8 relative to the stationary member 704C.

An example embodiment of the button assembly 50 will now be described with regard to FIGS. 7, 9F and 9G.

As mentioned above, FIG. 7 illustrates the portion of the first engagement mechanism 212 when the handle 224 is in the engaged position. FIG. 9F illustrates the button assembly 50 secured to an inner surface of the rail clamp body 212H. FIG. 9G is a cross-sectional view of the button assembly 50 through the middle portion of the button 500.

Referring to FIGS. 7, 9F and 9G, the button 500 has a T-shape including a first longitudinal portion 500_1 and a second touch portion 500_2 at a first end of the first longitudinal portion 500_1. The button 500 further includes a flange 503 at a second end of the first longitudinal portion 500_1. A helical spring 500S (referred to herein as a spring) is wrapped around the first longitudinal portion 500_1 of the button 500, and the button 500 and the spring 500S are arranged in a housing 500H. The spring 500S provides a bias force to maintain the button 500 in the unpressed position at rest until a force is applied by the user to press the button 500.

The housing 500H has a first cavity 510_1 and a second cavity 510_2. In the example embodiment shown in FIG. 9G, the first cavity 510_1 is larger in diameter than the second cavity 510_2 and positioned closer to the rail clamp body 212H when assembled. A first stopper 508, in the form of a notch, is included at an end of the second cavity 510_2 to retain the button 500 within the housing 500H when the button 500 is released and held in the rest position by the bias of the spring 500S. A spacer 504 is arranged in the first cavity 510_1 and configured to slide between a rest (locked) position and a pressed (unlocked) position when the button 500 is pressed by a user. A diaphragm button seal 506 is arranged about the outer surface of the spacer 504 to at least partially seal the opening through which the button 500 is inserted.

Example operation of first engagement mechanism 212 including the button assembly 50 will now be described with regard to FIGS. 6A-7 and 9G.

Referring to FIGS. 6A-7 and 9G, when in the rest (or unpressed) position, the button 500 is biased by the spring 500S towards the outer surface of the rail clamp body 212H and the rocker mount 700C is maintained in the locked or rest position. The end surface of the first longitudinal portion 500_1 of the button 500 may abut a surface of the movable member 702C of the rocker mount 700C in the rest position.

When the user presses the button 500 inward toward the table side of the first engagement mechanism 212, the force exerted on the button 500 causes the movable member 702C to pivot and rotate clockwise about the pin PIN_8 (1A in FIG. 7). The rotation of the movable member 702C causes the lock linkage 604 to move linearly towards the crank lock assembly 606 (2A and 3A in FIG. 7). The linear movement of the lock linkage 604 causes the lock hook 610 to pivot and rotate about the pin PIN_6 (4A in FIG. 7), thereby disengaging the hook portion 700F from the notch 702D in the longitudinal shaft portion 700D.

Once the button 500 is released, the components move in the opposite directions 1B, 2B, 3B and 4B shown in FIG. 7 as a result of the respective spring biases on the respective components of the locking assembly.

Actuation of the first engagement mechanism 212 from the disengaged position to the engaged position and then from the engaged position to the disengaged position after unlocking will now be described.

To move from the disengaged position (FIG. 6A) to the engaged position (FIG. 6B) to attach the table attach support 210 to the patient table 18, a user rotates the handle 224 clockwise approximately 180 degrees from the disengaged position to the engaged position. In this case, as the user rotates the handle 224 clockwise about a longitudinal axis of the longitudinal shaft portion 700D, the first linkage 244 and the first roller cam assembly 2180 operatively move first paddle 214_1 in a first direction (e.g., clockwise) about the first paddle post POST_4 into contact with an outer surface of a rail of the patient table 18. Concurrently and/or simultaneously, the second linkage 246, the reverse rocker 228, the third linkage 250 and the roller cam assembly 2200 operatively move second paddle 214_2 in a second direction (e.g., counterclockwise), which is opposite the first direction, about the second paddle post POST_5 into contact with the outer surface of the rail of the patient table 18. Similarly, the first roller cam assembly 2180 and the second roller cam assembly 2200 also rotate in opposite directions (e.g., counterclockwise and clockwise, respectively) about respective vertical posts (or cam shafts) POST_1 and POST_3 as the handle 224 is moved from the disengaged position to the engaged position.

As the handle 224 is moved (e.g., by a user) from the disengaged position toward the engaged position (e.g., as shown in FIG. 6C), the first guide roller 242_1 moves amongst the different profiles and transition regions of the first paddle 214_1 to the fully engaged position. The first roller cam 218_1 is also moved from a position in which the first roller cam 218_1 is not in contact with a lower surface of the rail 104 (FIG. 1) to a position in which first roller cam 218_1 is in contact with the lower surface of the rail 104. Similarly, the second guide roller 242_2 moves amongst the different profiles and transition regions of the second paddle 214_2 to the fully engaged position. The second roller cam 218_2 is also moved from a position in which the second roller cam 218_2 is not in contact with the lower surface of the rail to a position in which second roller cam 218_2 is in contact with the lower surface of the rail.

As the roller cams 218_1 and 218_2 engage with the lower surface of the rail 104, the frustoconical portions of the roller cams first contact a lower surface of the rail 104 and the roller cams 218_1 and 218_2 rotate about their respective longitudinal axes as the roller cams continue to contact the lower surface of the rail 104. In the fully engaged position (FIG. 6B), the second conical portions of the roller cams 218_1 and 218_2 are in contact with lower surface of the rail 104 thereby securing the table attach support 210 to the patient table 18.

As the handle 224 is moved from the disengaged position to the engaged position the hook portion 700F may press against (and potentially slide along) the longitudinal shaft portion 700D as a result of a spring bias (not shown) until finding and engaging with the notch 702D in the engaged position to lock the first engagement mechanism 212 and the table attach support 210 and to prevent release of the table attach support 210 until being unlocked by pressing button 500.

When removing the table attach support 210 from the patient table 18, once the hook portion 700F is disengaged from the notch 702D by pressing the button 500, the user rotates the handle 224 counterclockwise from the engaged position (FIG. 6B) to the disengaged position (FIG. 6A) to release the table attach support 210 from the patient table 18. As the user rotates the handle 224 counterclockwise about the longitudinal axis of the longitudinal shaft portion 700D, the first roller cam assembly 2180 and the second roller cam assembly 2200 rotate in opposite directions (e.g., clockwise and counterclockwise, respectively) about respective vertical posts (or cam shaft) POST_1 and POST_3 to return to the disengaged position shown in FIG. 6A. As the first roller cam assembly 2180 rotates, spring bias causes the first paddle 214_1 to return to the disengaged position shown in FIG. 6A. Concurrently or simultaneously, as the second roller cam assembly 2200 rotates, spring bias causes the second paddle 214_2 to return to the disengaged position shown in FIG. 6A.

According to one or more example embodiments, once the user releases the button 500, the bias force of the spring 500S moves the button 500 back to the rest position thereby resulting in the hook portion 700F rotating back to the locked position. The user need not hold the button 500 during the entire rotation of the handle 224 from the engaged to the disengaged position. Rather, once having disengaged the hook portion 700F from the notch 702D, the user may release the button 500 to allow the hook portion 700F to press against (and potentially slide along) the longitudinal shaft portion 700D until finding a notch on the opposing side of the longitudinal shaft portion 700D.

Although described herein with regard to the handle 224 and the button 500 positioned at the left rear of the first engagement mechanism 212, example embodiments should not be limited to these examples. Rather, mechanisms other than the handle 224, other positions of the button 500 and/or other lock/unlock mechanisms may be used.

Figure 10:
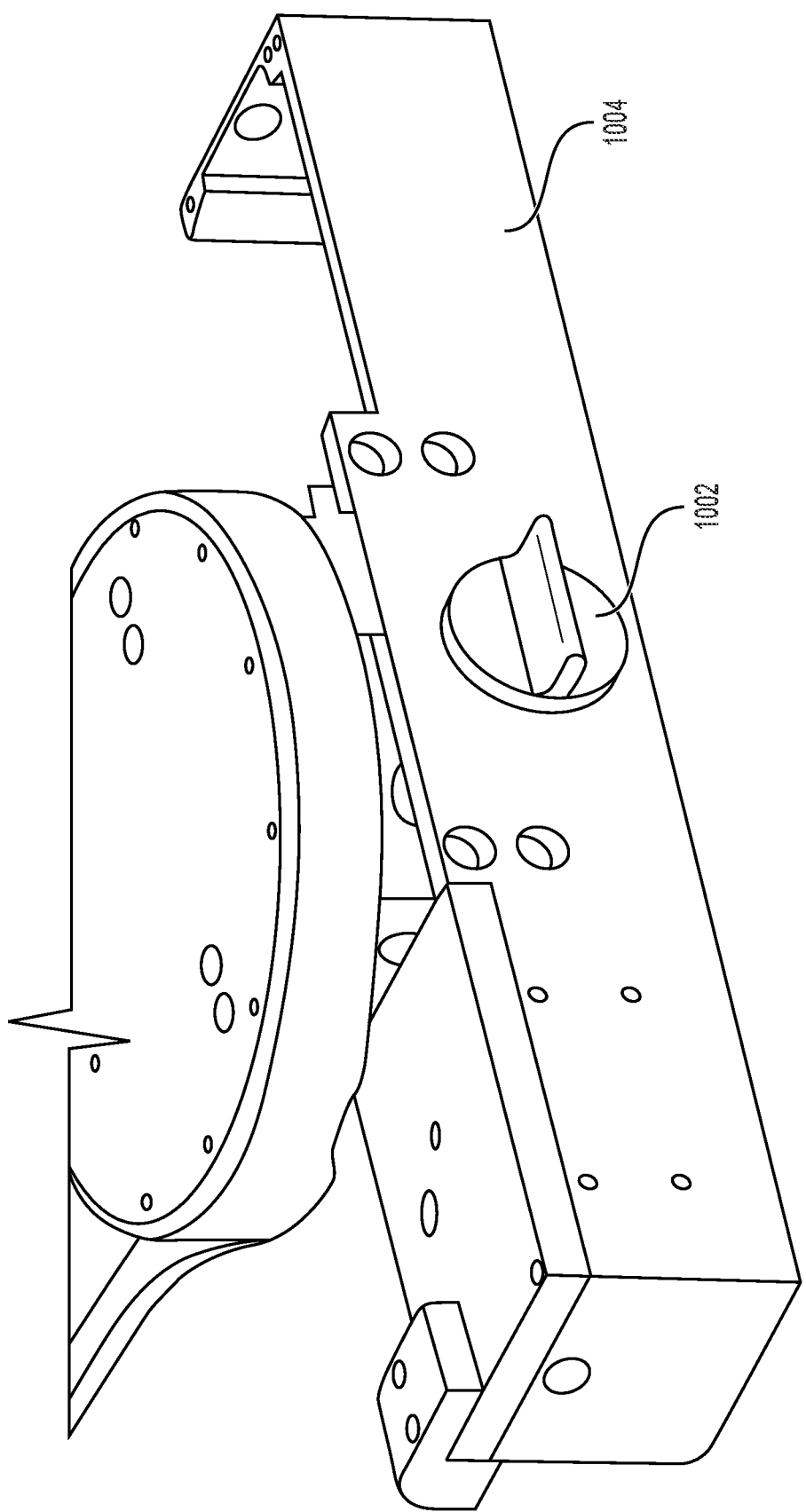
FIG. 10 is a rear perspective view of a table attach support according to other example embodiments.

For example, FIG. 10 illustrates an example embodiment in which the handle 224 is replaced with a turn knob 1002 arranged at the rear portion of the rail clamp housing 1004. In this example, the turn knob 1002 may be rotated clockwise or counterclockwise to engage and/or disengage an engagement mechanism with a patient table (e.g., patient table 18). In this example embodiment, the engagement mechanism may be similar or substantially similar to the first engagement mechanism 212 discussed herein, but with changes to accommodate the turn knob 1002.

FIGS. 11A and 11B illustrate an example embodiment in which the handle 224 is replaced with a sliding lever 1102 arranged between the upper surface of the rail clamp housing 1104 and the base 1106. In this example, the sliding lever 1102 slides between an engaged and disengaged position to engage and disengage an engagement mechanism to and from a patient table (e.g., patient table 18). In this example embodiment, the engagement mechanism may be similar or substantially similar to the first engagement mechanism 212 discussed herein, but with changes to accommodate the sliding lever 1102.

Figure 12:
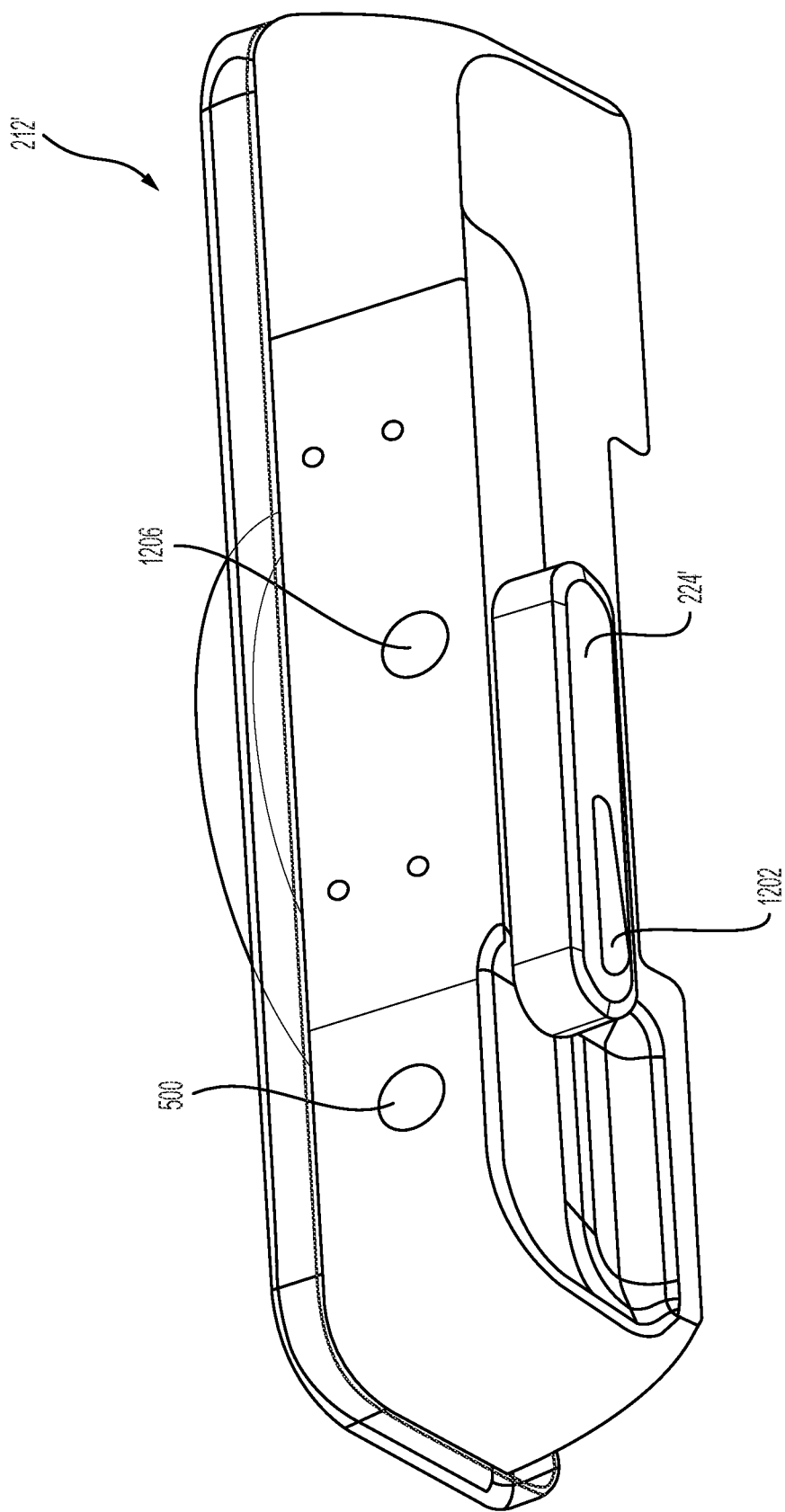
FIG. 12 is a rear perspective view of a table attach support according to other example embodiments.
Figure 13:
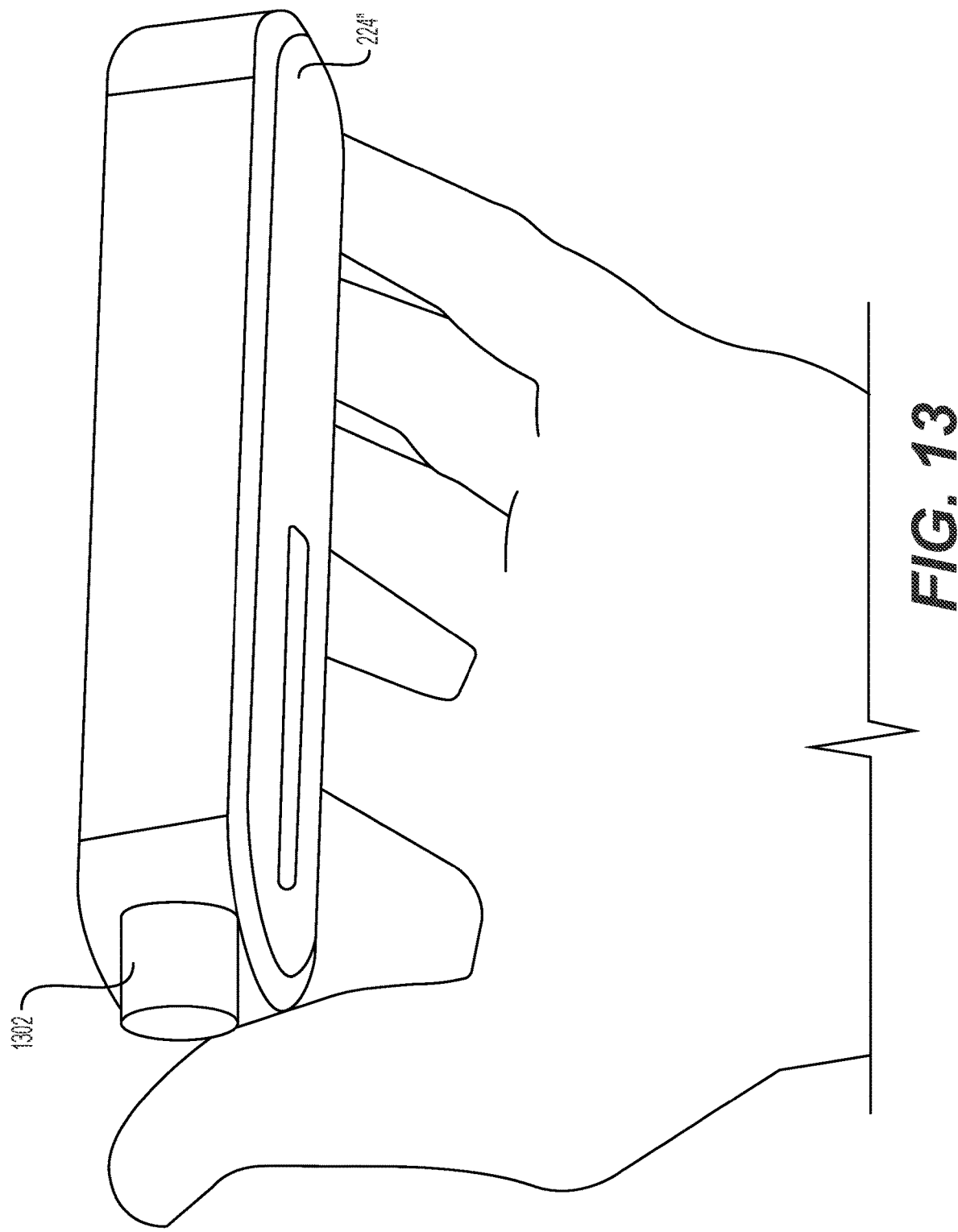
FIG. 13 is a rear perspective view of a handle having a lock button for a table attach support according to other example embodiments.

FIGS. 12 and 13 illustrate alternative positions for the button 500 according to example embodiments. For comparison, the position of the button 500 is also shown in FIG. 12.

As shown in FIG. 12, in one example, a button 1206 may be positioned at the center portion of the rear of the first engagement mechanism 212'. In yet another example, a button 1202 may be included as part of the handle 224' of the first engagement mechanism 212'. In this example, the button 1202 is positioned on the underside of the handle 224'

In FIG. 13, the button 1302 is positioned on the side portion of the handle 224".

As mentioned above, one or more example embodiments provide a catheter-based procedure system or other medical device procedure system having ergonomic and/or balanced touchpoints to enable a user to lift and place the system directly on the patient table 18. The touchpoints are designed such that the user's hands are away from pinch zones and will not require the need to change grip when placing/removing.

Figure 14:
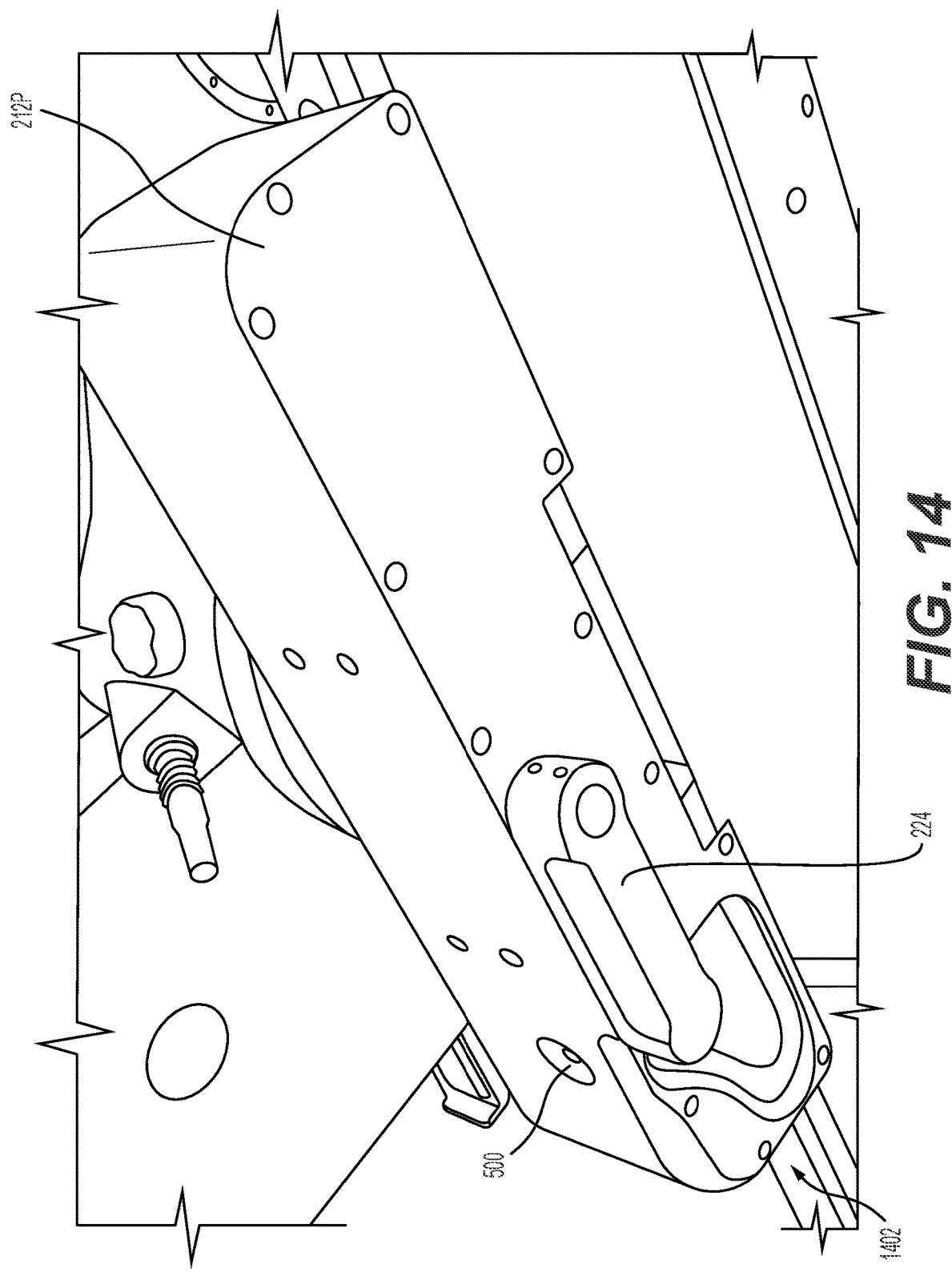
FIG. 14 is another perspective view of a portion of the table attach support shown in FIGS. 4A and 4B.
Figure 15:
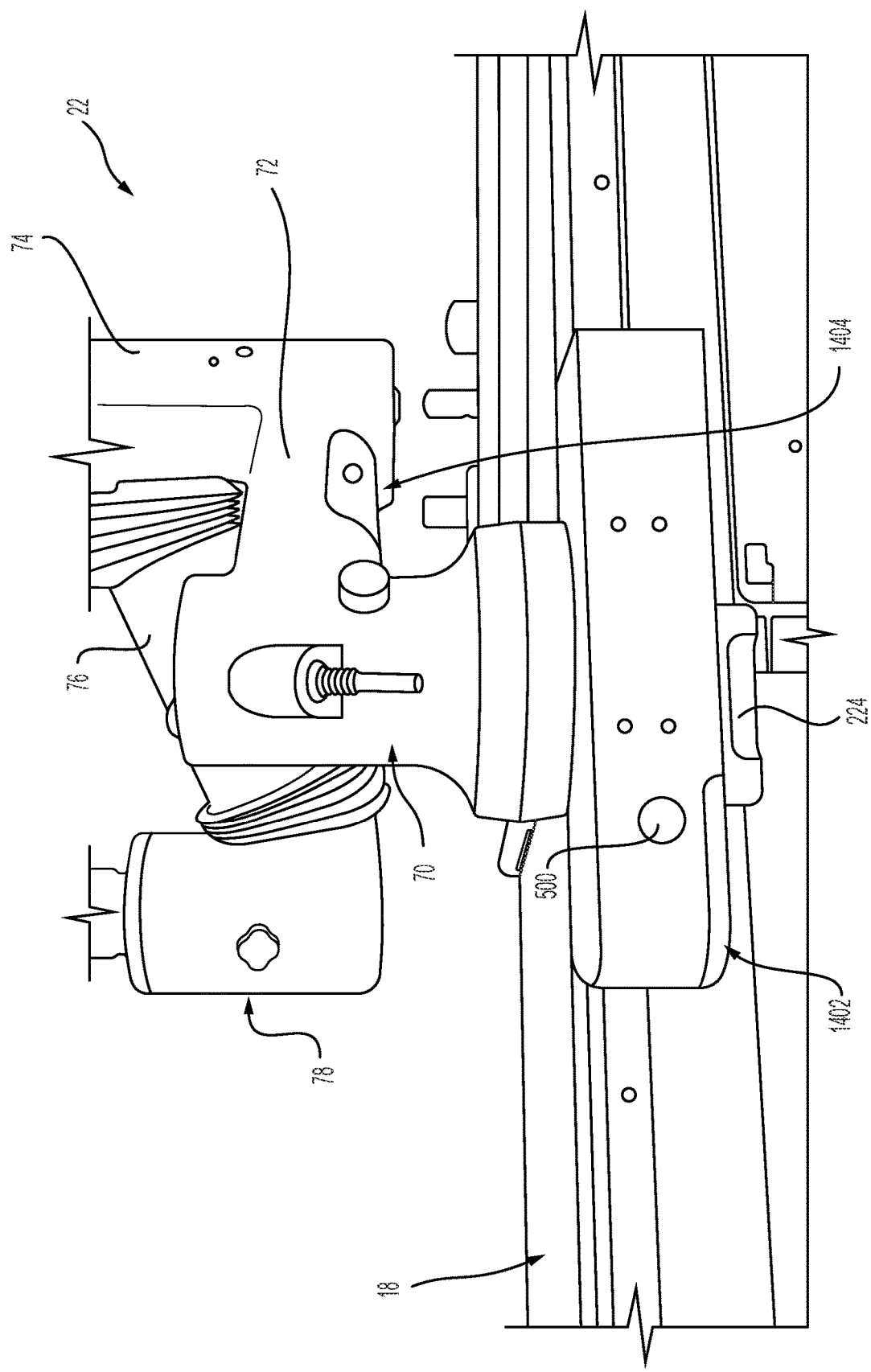
FIG. 15 is a rear view of a table attach support engaged with a table, according to example embodiments.

FIG. 14 is a bottom perspective view of the first engagement mechanism 212 and FIG. 15 is a rear view of the first engagement mechanism 212 and positioning system 22 for the robotic drive 24.

As shown in FIG. 14, the rail clamp plate 212P includes the first grip 502 on the bottom side thereof to aid and/or guide the user in lifting the positioning system 22 for attachment to and/or removal from the patient table 18. The first grip 502 may be an ergonomic grip and balanced touch point. The first grip 502 is positioned away from pinch zones of the first engagement mechanism 212 and the positioning system 22 thereby avoiding the need to change grip when place and/or removing the positioning system 22 on the patient table 18. The first grip 502 may be contoured to accommodate gripping by the user when lifting the positioning system 22 (e.g., with the user's palm facing up).

As shown in FIG. 15, the positioning system 22 includes various segments and joints coupling to allow the robotic drive 24 (FIG. 1) to be positioned as desired, for example, relative to the patient. The positioning system 22 includes a first rotational joint 70 coupled to the first engagement mechanism 212. The first rotational joint 70 allows rotation of a first arm 72, or link, about a rotational axis. In the illustrated example, the rotational axis is substantially vertical and runs through the center of the first rotational joint 70. The first rotational joint 70 can include circuitry to allow a user to control the rotation of the first rotational joint 70.

The first arm 72 is substantially horizontal with a first end coupled to the first rotational joint 70. The second end of the first arm 72 is coupled to a second rotational joint 74. The first arm 72 includes a second grip or balanced touch point 1404 to aid in lifting the positioning system 22 for attachment to and/or removal from the patient table 18. As with the first grip 1402, the second grip 1404 is also positioned away from pinch zones of the positioning system 22 thereby avoiding the need to change grip when place and/or removing the positioning system 22 on the patient table 18. As with the first grip 502, the second grip 1404 may be contoured to accommodate gripping by the user when lifting the positioning system 22 (e.g., with the user's palm facing up).

Still referring to FIGS. 14 and 15, the second rotational joint 74 is also coupled to a first end of a second arm 76. Thus, the second rotational joint 74 allows rotation of the second arm 76 relative to the first arm 72. As with the first rotational joint 70, the second rotational joint 74 allows rotation about a substantially vertical axis running through the center of the second rotational joint 74. Further, the second rotational joint 74 may include circuitry to allow a user to control the rotation of the second rotational joint 74.

In the illustrated example, a second end of the second arm 76 is coupled to a third rotational joint 78. The third rotational joint 78 includes a post 80 to allow mounting of the robotic drive 24 to the positioning system 22. Thus, the third rotational joint 78 allows rotation of the robotic drive 24 relative to the second arm 76. The third rotational joint 78 allows rotation about a substantially vertical axis running through the center of the third rotational joint 78. Further, the third rotational joint 78 can include circuitry to allow a user to control the rotation of the third rotational joint 78.

In one example, the second arm 76 includes a 4-arm linkage which can allow limited vertical movement of third rotational joint 78 relative to the second rotational joint 74. In this regard, the 4-arm linkage can allow vertical movement of the third rotational joint 78, while maintaining the substantially vertical orientation of the third rotational joint 78 and the post 80.

Although the table attach support according to example embodiments is described herein with regard to being attached to the patient table 18 shown in FIG. 1, example embodiments should not be limited to this example.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

Although the present disclosure has been described with reference to example embodiments, workers skilled in the art will recognize that changes may be made in form and detail without departing from the spirit and scope of the defined subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described is manifestly intended to be as broad as possible. For example, unless specifically otherwise noted, the definitions reciting a single particular element also encompass a plurality of such particular elements.

What is claimed is:

1. A table attach support to secure a medical device to a patient table having a patient supporting surface, the table attach support comprising:
    a first engagement mechanism including an attachment mechanism and a locking mechanism;
    a second engagement mechanism;
    an extension member extending between the first engagement mechanism and the second engagement mechanism; wherein
        the attachment mechanism is configured to actuate from a first position to a second position to secure the table attach support to the patient table, and
        the locking mechanism is configured to lock the attachment mechanism in the second position, and
        the locking mechanism includes a release button configured to, when pressed, unlock the attachment mechanism to enable actuation of the attachment mechanism from the second position to the first position to release the table attach support from the patient table; and
    a handle configured to cause the attachment mechanism to actuate from the second position to the first position when unlocked.

2. The table attach support of claim 1, wherein, when unlocked, the attachment mechanism is configured to remain in the second position with the table attach support secured to the patient table until actuated from the second position to the first position via movement of the handle.

3. A table attach support, to secure a medical device to a patient table having a patient supporting surface, the table attach support comprising:
    a first engagement mechanism including an attachment mechanism and a locking mechanism;
    a second engagement mechanism; and
    an extension member extending between the first engagement mechanism and the second engagement mechanism; wherein
        the attachment mechanism is configured to actuate from a first position to a second secure the table attach support tot be patient table,
        the locking mechanism is configured to lock the attachment mechanism in the second position, and
        the attachment mechanism includes
            a first roller cam assembly,
            a second roller cam assembly, and
            a linkage assembly operatively coupled to the first roller cam assembly and the second roller cam assembly, the linkage assembly configured to cause the first roller cam assembly and the second roller cam assembly to move in opposite directions during actuation from the first position to the second position or from the second position to the first position.

4. The table attach support of claim 3, wherein
    the locking mechanism includes a crank lock assembly engaged with the linkage assembly;
    the table attach support includes a handle engaged with the crank lock assembly, the handle configured to cause the attachment mechanism to actuate from the first position to the second position or from the second position to the first position; and
    the crank lock assembly is configured to
        translate movement of the handle into movement of the attachment mechanism to move the attachment mechanism between the first position and the second position, and
        lock the attachment mechanism in the second position.

5. The table attach support of claim 4, wherein the crank lock assembly comprises:
    a crank including having a longitudinal shaft portion and a flange portion engaged with the linkage assembly, the longitudinal shaft portion having a notch, and the crank being configured to translate the movement of the handle into the movement of the attachment mechanism; and
    a lock hook configured to engage with the notch to lock the attachment mechanism in the second position.

6. The table attach support of claim 5, wherein the notch is on a surface of the longitudinal shaft portion of the crank.

7. The table attach support of claim 5, wherein the locking mechanism comprises:
    a lock button assembly and a lock linkage configured to disengage the lock hook from the notch to unlock the attachment mechanism thereby allowing movement from the second position to the first position.

8. The table attach support of claim 7, wherein the crank lock assembly comprises:
    a body member having a cylindrical hole and a slot, the cylindrical hole configured to receive the longitudinal shaft portion of the crank, and the slot configured to receive the lock hook, and wherein
    the lock hook is pivotably secured in the slot via a pin.

9. The table attach support of claim 8, wherein the lock hook is configured to pivot about the pin to move between an engaged position, in which the lock hook is engaged with the notch, and a disengaged position, in which the lock hook is disengaged from the notch.

10. The table attach support of claim 9, wherein
    the lock button assembly includes
        a release button, and
        a rocker mount engaged with the lock linkage, the rocker mount configured to translate pressing of the release button into force exerted on the lock linkage; and
    the lock linkage is pivotably engaged with the lock hook, and the lock linkage is configured to cause the lock hook to pivot in response to the force exerted by the rocker mount.

11. A table attach support to secure a medical device to a patient table having a patient supporting surface, the table attach support comprising:
    a first engagement mechanism including an attachment mechanism and a locking mechanism;
    a second engagement mechanism; and an extension member extending between the first engagement mechanism and the second engagement mechanism; wherein
the attachment mechanism is configured to actuate from a first position to a second position to secure the table attach support to the patient table,
the locking mechanism is configured to lock the attachment mechanism in the second position,
the first engagement mechanism includes a housing having an upper housing part and a lower housing part,
the attachment mechanism and the locking mechanism are arranged inside the housing,
the locking mechanism is arranged on an inside of the upper housing part and on an inside of the lower housing part, and
the attachment mechanism is arranged on the inside of the lower housing part.

12. The table attach support of claim 11, wherein the first engagement mechanism comprises:
a user grip or touch point arranged on an outside of an underside of the lower housing part.

13. A medical device comprising:
a robotic drive;
a positioning system configured to support the robotic drive; and
a table attach support configured to support the positioning system, and to secure the medical device to a patient table having a patient supporting surface, the table attach support including
a first engagement mechanism including an attachment mechanism and a locking mechanism,
a second engagement mechanism,
an extension member extending between the first engagement mechanism and the second engagement mechanism, wherein
the attachment mechanism is configured to actuate from a first position to a second position to secure the table attach support to the patient table,
the locking mechanism is configured to lock the attachment mechanism in the second position, and
the locking mechanism includes a release button configured to, when pressed, unlock the attachment mechanism to enable actuation of the attachment mechanism from the second position to the first position to release the table attach support from the patient table, and
a handle configured to cause e attachment mechanism to actuate from the second position to the first position when unlocked.

14. The medical device of claim 13, wherein, when unlocked, the attachment mechanism is configured to remain in the second position with the table attach support secured to the patient table until actuated from the second position to the first position via movement of the handle.

15. The medical device of claim 13, wherein the attachment mechanism comprises:
a first roller cam assembly;
a second roller cam assembly; and
a linkage assembly operatively coupled to the first roller cam assembly and the second roller cam assembly, the linkage assembly configured to cause the first roller cam assembly and the second roller cam assembly to move in opposite directions during actuation from the first position to the second position or from the second position to the first position.

16. The medical device of claim 15, wherein
the locking mechanism includes a crank lock assembly engaged with the linkage assembly;
the handle is engaged with the crank lock assembly, and the handle is configured to cause the attachment mechanism to actuate from the first position to the second position; and
the crank lock assembly is configured to
translate movement of the handle into movement of the attachment mechanism to move the attachment mechanism between the first position and the second position, and
lock the attachment mechanism in the second position.

17. The medical device of claim 16, wherein the crank lock assembly comprises:
a crank including having a longitudinal shaft portion and a flange portion engaged with the linkage assembly, the longitudinal shaft portion having a notch, and the crank being configured to translate the movement of the handle into the movement of the attachment mechanism; and
a lock hook configured to engage with the notch to lock the attachment mechanism in the second position.

18. The table attach support of claim 17, wherein the locking mechanism comprises:
a lock button assembly and a lock linkage configured to disengage the lock hook from the notch to unlock the attachment mechanism thereby allowing movement from the second position to the first position, the lock button assembly including the release button.

19. A medical device comprising:
a robotic drive;
a positioning system configured to support the robotic drive; and
a table attach support configured to support positioning system, and to secure the medical device a patient table having a patient supporting surface, the table attach support including
a first engagement mechanism including an attachment mechanism and a locking mechanism,
a second engagement mechanism,
an extension member extending between the first engagement mechanism and the second engagement mechanism, wherein
the attachment mechanism is configured to actuate from a first position to a second position to secure the table attach support to the patient table,
the locking mechanism is configured to lock the attachment mechanism in the second position,
the first engagement mechanism includes a housing in which the attachment mechanism and the locking mechanism are arranged, and
the medical device includes a first user grip or touch point arranged on an outside of an underside of the housing.

20. The medical device of claim 19, wherein
the positioning system includes a plurality of arms and rotational joints for positioning the robotic drive;
a first of the plurality of arms having a first end coupled to a top portion of the table attach support; and
the first of the plurality of arms includes a second user grip or touch point.

* * * * *